United States Patent
Ouvrier-Buffet et al.

(10) Patent No.: US 9,885,674 B2
(45) Date of Patent: Feb. 6, 2018

(54) METHOD AND DEVICE FOR RECOGNITION OF A MATERIAL MAKING USE OF ITS TRANSMISSION FUNCTION

(75) Inventors: Patrice Ouvrier-Buffet, Saint-Jorioz (FR); Guillaume Beldjoudi, Grigny (FR); Veronique Rebuffel, Corenc (FR); Jean Rinkel, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 1172 days.

(21) Appl. No.: 13/514,802

(22) PCT Filed: Nov. 2, 2010

(86) PCT No.: PCT/EP2010/066652
§ 371 (c)(1),
(2), (4) Date: Jun. 8, 2012

(87) PCT Pub. No.: WO2011/069748
PCT Pub. Date: Jun. 16, 2011

(65) Prior Publication Data
US 2012/0239310 A1 Sep. 20, 2012

(30) Foreign Application Priority Data
Dec. 9, 2009 (FR) .................................. 09 58804

(51) Int. Cl.
*G01N 23/083* (2006.01)
*G06F 19/00* (2011.01)
*G01N 23/087* (2006.01)

(52) U.S. Cl.
CPC .................................. *G01N 23/087* (2013.01)

(58) Field of Classification Search
CPC ..... G01N 23/083; G01N 23/087; G06F 19/00
(Continued)

(56) References Cited

U.S. PATENT DOCUMENTS 5,204,889 A * 4/1993 Kraybill ............... G01B 15/025
378/51
5,206,174 A 4/1993 Gehrke et al.
(Continued)

FOREIGN PATENT DOCUMENTS

CN 1995993 A 7/2007
EP 2 071 722 A1 6/2009
(Continued)

OTHER PUBLICATIONS

Search Report dated Jul. 21, 2010 in France Patent Application No. FA732709 FR 0958804 (with English translation of category of cited documents).
ANSI N42.14-1999 "American National Standard for Calibration and use of Germanium Spectrometers for the Measurement of Gamma-Ray Emission Rates of Radionuclides", ANSI N42.14-1999 (revision of ANSI N42.14-1991), 1999, American National Standards Institutes, pp. 7,13,15,86,89,134.
(Continued)

*Primary Examiner* — John Breene
*Assistant Examiner* — Peter Ngo
(74) *Attorney, Agent, or Firm* — Oblon, McClelland, Maier & Neustadt, L.L.P.

(57) ABSTRACT

A method for characterizing nature of a material, including: providing at least one sample of the material between an X-ray source and a detector; using the X-ray source to make N X-radiation spectra transmitted through the material, each for a time; calculating transmission function of the material as a function of energy or the detection channel; and in each of at least two energy zones, calculating the integral of the transmission function, thus forming at least a first transmission coefficient and a second transmission coefficient.

20 Claims, 16 Drawing Sheets

(58) Field of Classification Search
USPC .......................................................... 702/32
See application file for complete search history.

(56) References Cited

U.S. PATENT DOCUMENTS

| | | | |
|---|---|---|---|
| 5,821,538 A | 10/1998 | De Antoni et al. | |
| 6,018,562 A | 1/2000 | Willson | |
| 7,260,171 B1* | 8/2007 | Arenson | A61B 6/032 378/16 |
| 7,580,505 B2 | 8/2009 | Kang et al. | |
| 2003/0033097 A1 | 2/2003 | Tanaka et al. | |
| 2007/0147585 A1* | 6/2007 | Eilbert | G01N 23/04 378/57 |
| 2008/0025385 A1 | 1/2008 | Barat et al. | |
| 2009/0152448 A1 | 6/2009 | Ouvrier-Buffet et al. | |
| 2011/0098980 A1 | 4/2011 | Ouvrier-Buffet et al. | |

FOREIGN PATENT DOCUMENTS

| | | |
|---|---|---|
| FR | 2 738 693 A1 | 3/1997 |
| FR | 2 870 603 A1 | 11/2005 |
| GB | 2 433 777 A | 7/2007 |
| JP | 2002-350545 A | 12/2002 |
| JP | 2008-513740 A | 5/2008 |
| JP | 2010-537163 A | 12/2010 |
| JP | 2011-521208 A | 7/2011 |
| WO | WO 2006/029475 A1 | 3/2006 |
| WO | WO 2008/142446 A2 | 11/2008 |
| WO | WO 2009/024817 A1 | 2/2009 |
| WO | WO 2009/024818 A1 | 2/2009 |
| WO | WO 2009/130492 A1 | 10/2009 |

OTHER PUBLICATIONS

Lucian Wielopolski, et al., "Prediction of the Pulse-Height Spectral Distortion Caused by the Peak Pile-Up Effect", Nuclear Instruments and Methods, 133, 1976, pp. 303-309.
U.S. Appl. No. 13/535,852, filed Jun. 28, 2012, Brambilla, et al.
U.S. Appl. No. 14/677,293, filed Apr. 2, 2015, Popa, et al.
English Translation of the International Preliminary Report on Patentability dated Aug. 9, 2012, in PCT/EP2010/066652.
V. D. Ryzhikov, et al., "A spectrometric approach in radiography for detection of materials by their effective atomic number", Nuclear Intruments and Methods in Physics Research A, vol. 603, No. 3, XP 026097538, Feb. 2009, pp. 349-354.
Sergey V. Naydenov, et al., "Direct reconstruction of the effective atomic number of materials by the method of multi-energy radiography", Nuclear Intruments and Methods in Physics Research B, vol. 215, No. 3-4, XP 004486776, Feb. 2004, pp. 552-560.
L. A. Lehmann, et al., "Generalized image combinations in dual KVP digital radiography", Medical Physics, vol. 8, No. 5, XP 002631532, Sep./Oct. 1981, pp. 659-667.
Office Action dated Aug. 25, 2014 in Japanese Patent Application No. 2012-542421 (with English language translation).
Thomas Trigano, "Traitement statistique du signal spectrométrique: étude du désempilement de spectre en énergie pour la spectrométrie Gamma", LTCI—Télécom ParisTech, Version 1, Jul. 11, 2006, 179 pages (with English abstract).
Decision of Rejection dated Jul. 13, 2015 in Japanese Patent Application No. 2012-542421 (with English language translation).

* cited by examiner

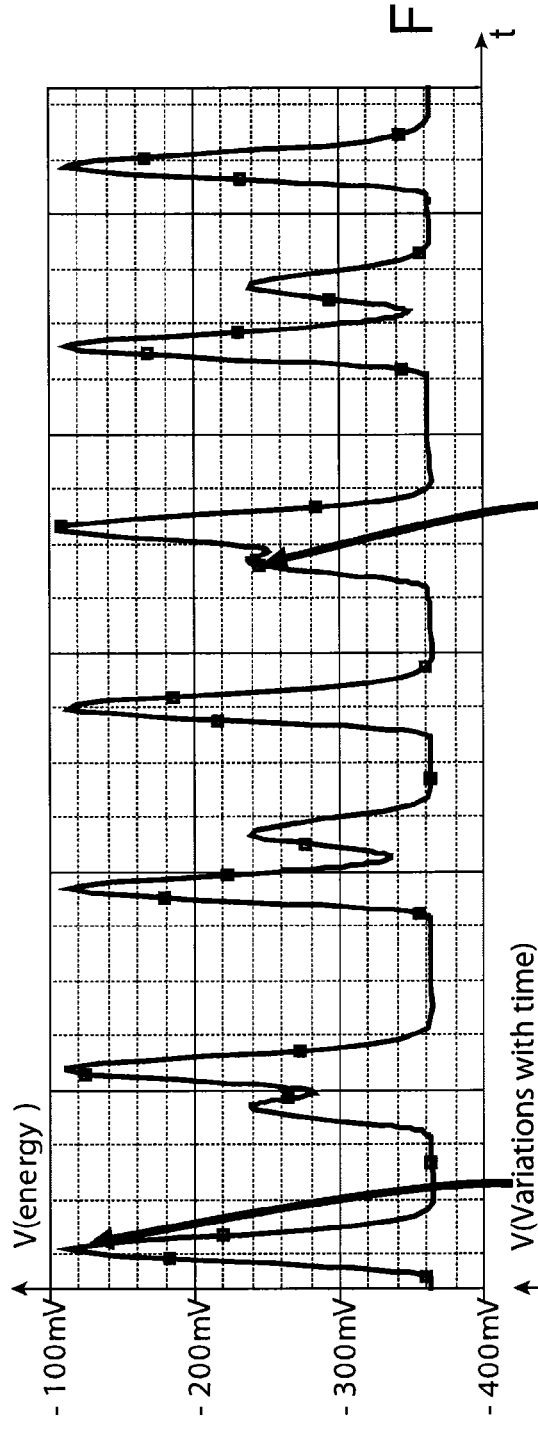
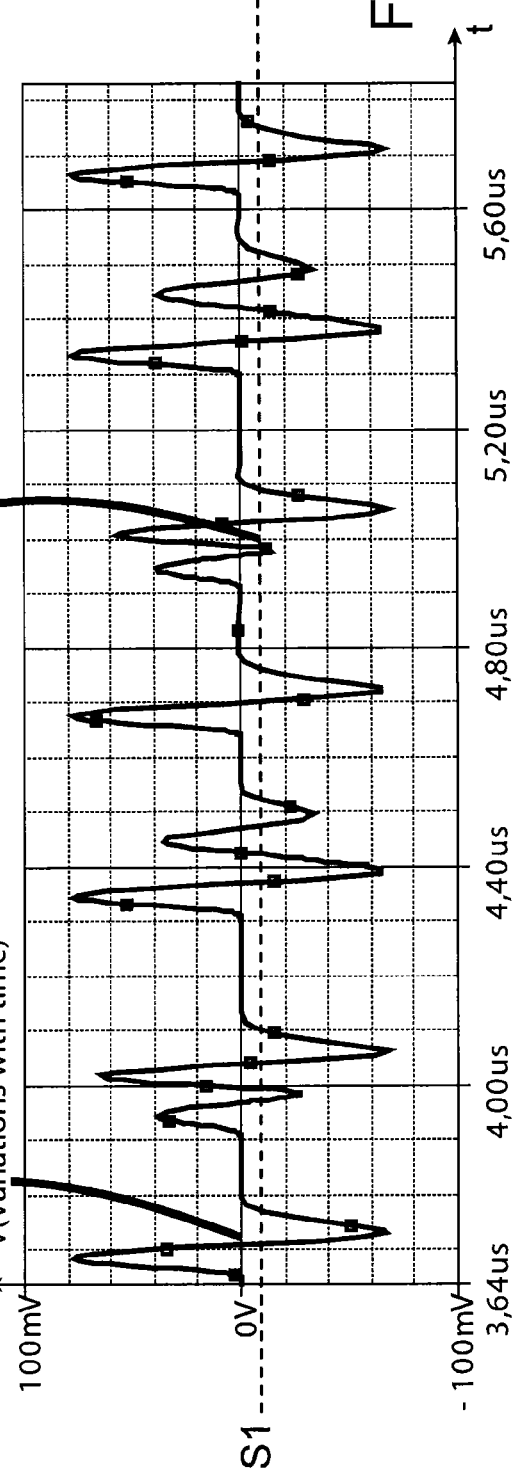
FIG.22A
FIG.22B

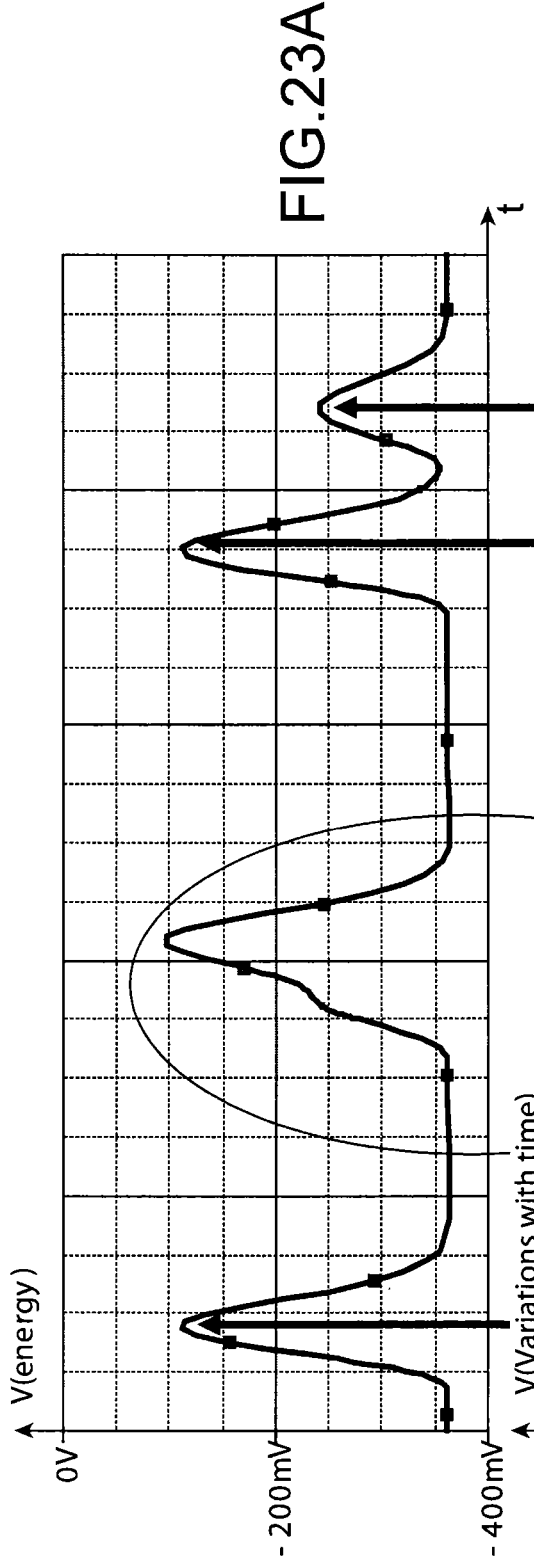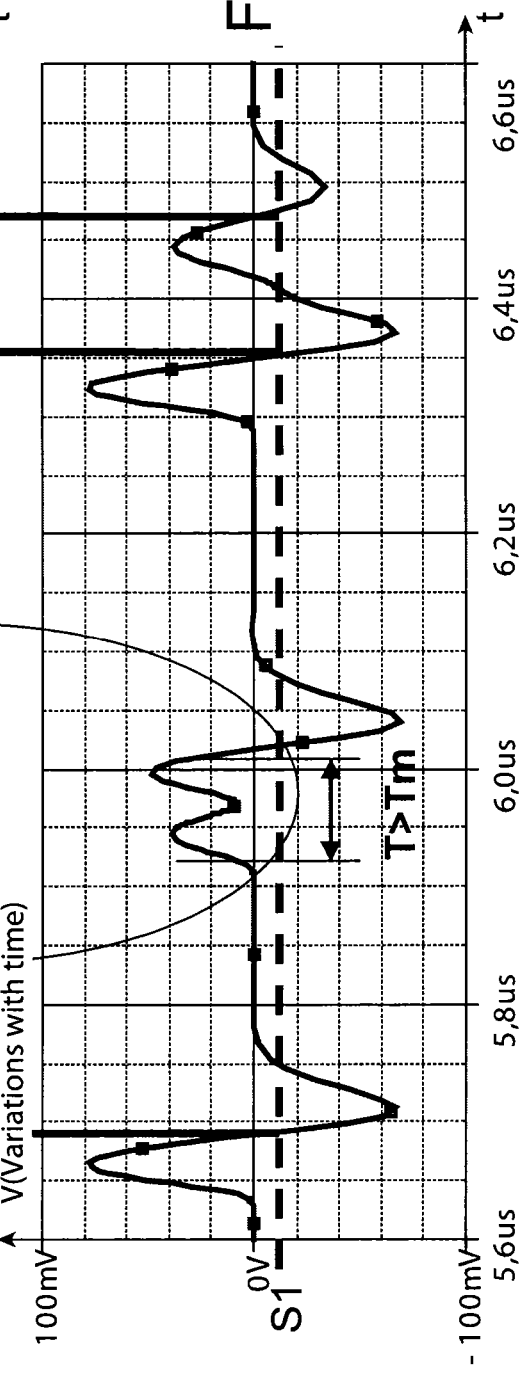

METHOD AND DEVICE FOR RECOGNITION OF A MATERIAL MAKING USE OF ITS TRANSMISSION FUNCTION

TECHNICAL FIELD AND PRIOR ART

The invention relates to the field of material analysis techniques, for example to identify products such as explosive in luggage, starting from analysis of the X-radiation transmission function of this luggage.

Therefore it has applications in systems used in airports to identify explosive materials in luggage.

But other applications may relate to domains in which it is required to quickly determine the nature of a material making use of radiation.

According to known luggage inspection techniques, an X-radiation source, generally an X-ray tube, produces radiation that passes through the luggage.

According to a first technique, several views of the luggage are made using a scanner or another device in order to count the number of photons that pass through the object by different paths.

With this method, variations in transmission are measured as a function of the thickness through which the X-rays have passed, and sophisticated algorithms are used to determine the nature of the object observed.

A second technique consists of using two sources of monochromatic X-rays or two X-ray tubes adjusted to two different acceleration voltages. Either of these two sources is switched.

These two beams can be used to obtain approximate data on a low energy channel and a high energy channel, making use of a discrimination and counting system.

According to a third technique, the X radiation is detected by a detector in the form of a strip (linear assembly) of detectors.

The detectors are usually scintillation detectors, for example CsI(Tl) crystals coupled to photo-multipliers.

Existing systems called Sandwich systems are composed of 2 layers of detectors superposed one on the other (double layer), and separated by a thickness of an intermediate material forming a filter with the first detector attenuating lower energy photons.

Thus, the first layer that is usually very thin, is more sensitive to low energy photons while the second layer which is thicker detects a hardened spectrum, the lower energy photons having been attenuated by the intermediate material.

Although the second detector outputs data representative of high energy (H.E.) while the first outputs a signal representative of low energy (L.E.), it results in a very low energy separability due to the overlap of the H.E. and L.E signals. Furthermore, this system cannot be generalised to more than two energies (HE, LE).

According to prior art, only two magnitudes are measured, one corresponding to a low energy count and the other corresponding to a high energy count. The result is lack of precision. Furthermore, for a given system, the energy ranges corresponding to the two magnitudes cannot be configured.

Another disadvantage of this technique is the use of two detectors to make a measurement. Thus, if N measurements are to be made, for example along a line, then 2N detectors have to be used.

PRESENTATION OF THE INVENTION

Therefore, the inventors chose to use a different measurement method based on the possible use of a single detector and a spectrometry technique, in other words the use of an amplitude distribution of pulses measured by the detector, rather than counting techniques.

But, there are technical difficulties in using such a solution. Known spectrometry techniques are difficult to make compatible with existing luggage inspection requirements; a fast method is needed that is also precise and compatible with safety. In particular, the advance rate of luggage necessitates making a measurement of the energy of the transmitted photons within a short period (a few ms) with a strong flux of high incident photons (fluence between a few Mphotons/mm$^2$/s and a few tens of Mphotons/mm$^2$/s) to keep the results statistically meaningful.

With spectrometry devices according to prior art, it is impossible to make useable spectra by applying such intense photon radiation to a detector within such a short time, particularly as a result of photon stacking problems.

A spectrum measurement was performed with two different fluxes, showing problems that arise as a result of the stacking phenomenon. A first curve corresponds to a flux of $6.082\times10^6$ photons/s/pixel while a second curve corresponds to a flux of $4.752\times10^4$ photons/s/pixel, the area covered by each pixel being 800 µm×800 µm with a depth of 3 mm.

When the flux increases (number of incident X photons per unit time per pixel), the signal provided degrades due to the stacking phenomenon: if the time lapse between two detected events is too short, the system is incapable of discriminating them and it outputs an incorrect signal that depends on the energies of the two photons and the time interval separating them.

Therefore, based on the above mentioned curves, two effects resulting from the stacking phenomenon could be evidenced:
  a reduction in the count when the flux increases, visible at low energies, and
  an increase in the number of events counted at high energies with the flux due to the stacked spectrum.

There are various classes of methods that can be used to deal with the stacking phenomenon.

Empirical methods are known; one approach is based on calibration of the stacking phenomenon using radioactive sources with known activity.

Information derived from the calibration is then used on the unknown signal, as described in the American National Standard for Calibration and Use of Germanium Spectrometers for the Measurement of Gamma-Ray Emission Rates of Radionuclides, American National Standards Institute (ANSI) N42.14-1999, p. 7, 13, 15, 86, 89, 134.

The main disadvantage of this approach is the need to have γ sources with high radioactive activity, which makes the calibration method complex and in particular creates radiation shielding problems.

Analogue methods are also known that optimise the electronics to minimise stacking. In particular, the use of inhibiting circuits means that there is no need to take account of new particles absorbed before the end of processing of the current particle. This type of approach can give a system that cannot be paralysed, the disadvantage being that the dead time resulting from processing reduces the performances of such a system in terms of the count rate.

There are also digital methods called active time correction methods that make it possible to reject part of stacking, and then to analyse the signal shape.

Finally, there are a posteriori correction methods particularly like that described in document FR 2 870 603 or described by Trigano, T., Traitement du signal spectrométrique: Etude du désempilement de spectre en énergie pour la spectrométrie gamma (Processing of the spectrometric signal: Study of energy spectrum destacking for gamma spectrometry). 2006. This method is based on knowledge of the duration and energy of each pulse.

The main purpose of this invention is to solve these problems.

The invention firstly relates to a method for characterising the nature of a material, consisting of the following steps:
provide at least one sample of this material between an X-ray source and a detector,
use the X-ray source to make at least one X-radiation spectrum transmitted through said material, each for a duration Δt, for example between 1 ms and 10 ms or between 100 μs and a few seconds, for example or 5 s or 10 s; each spectrum represents the intensity as a function of the energy or the detection channel,
calculate the transmission function of this material as a function of the energy or the detection channel,
in each of N (N≤2) energy bands (or zones) comprising a first energy band for example called the low energy zone, and a second energy band for example called the high energy zone, determine a coefficient of transmission corresponding to a statistical magnitude, for example the integral of the transmission function with respect to energy or the mean, thus forming at least a first transmission coefficient (α1) and a second transmission coefficient (α2).

The nature of the material can then be obtained by comparing transmission coefficients with standard transmission coefficients.

When N is equal to 2, the method may comprise:
selection of a first energy zone called the low energy zone, and a second energy zone called the high energy zone,
calculation of the integral of the transmission function with respect to energy, thus forming at least a first transmission coefficient (α1) and a second transmission coefficient (α2).

The first energy zone is preferably between 15 and 50 keV and the second energy zone may be between 50 and 120 keV.

The nature of said material can thus be determined using said statistical magnitudes or coefficients, for example by positioning calculated coefficients in a plane comprising coefficients of known materials, as a function of their thickness.

Preferably, the fluence rate of photons incident on the material is between $10^6$ photons $mm^{-2} \cdot s^{-1}$ and $10^7$ photons $mm^{-2} s^{-1}$.

A method according to the invention may comprise a prior step to measure the energy spectrum of radiation from the X-radiation source when there is no material inserted between this source and the detector.

A method according to the invention may also comprise a spectra correction step for disturbances resulting from stacking phenomena.

The invention also relates to a device to characterise the nature of a material sample, comprising:
an X-ray source, preferably to emit incident photon radiation for which the fluence rate is between $10^6$ $mm^{-2} \cdot s^{-1}$ and $10^7$ $mm^{-2} s^{-1}$,
a detector, for example a semiconductor or scintillation type detector or an ionisation chamber,
means of using the X-ray source to make an X radiation spectrum transmitted through this material, each for a time Δt,
means of calculating the transmission function of this material as a function of the energy or the detection channel,
means of calculating at least a first transmission coefficient ($α_1$) and a second transmission coefficient ($α_2$) in a first energy band called a low energy band and a second energy band called a high energy band respectively, each coefficient being a statistical magnitude such as the integral or mean of the transmission function in each energy band.

Means may be provided to determine the nature of said material, using these two coefficients.

Such a device, when N is equal to 2, may comprise means to:
select a first energy zone called the low energy zone, and a second energy zone called the high energy zone,
calculate the integral of the transmission function with respect to energy, and to form at least a first transmission coefficient (α1) and a second transmission coefficient (α2).

Such a device also preferably comprises mean of correcting spectra for stacking phenomena, for example:
means of determining a stacked spectrum (Emp), that is the part of the measured spectrum ($Sp_{mes}$) that corresponds to stacks alone,
means of calculating at least one first corrected spectrum ($Sp_{cor}$), by taking the difference between the measured spectrum ($Sp_{mes}$) and the stacked spectrum (Emp).

The stacked spectrum may be calculated using the measured spectrum ($Sp_{mes}$) and exposure time ($T_{expo}$) and dead time ($T_{dead}$) data for the system, the minimum time separating two photons below which only one of the two photons is detected.

Means may be provided to determine the dead time by simulation.

Such a device may comprise means of making the calculation of $N_{it}$ ($N_{it} \geq 1$) corrected spectra ($Sp_{cor(n)}$) starting from the corrected spectrum of order $Sp_{cor(n-1)}$, or from the measured spectrum if there is no previously corrected spectrum, by taking the difference between the corrected spectrum and the stacked spectrum (Emp). A method according to this invention can use this step.

Such a device may comprise means of performing the following steps iterated $N_{it}$ times where $N_{it} \geq 1$:
calculate the stacking probability as a function of the previously corrected spectrum $Sp_{cor(n-1)}$ in other words produced during the previous iteration, or the measured spectrum if there is no previously corrected spectrum, and exposure time ($T_{expo}$) and dead time ($T_{dead}$) data,
estimate a stacked spectrum (Emp) as a function of the previously corrected spectrum, or the measured spectrum if there is no previously corrected spectrum, and the dead time ($T_{dead}$),
calculate a corrected spectrum, for example by taking the difference between the measured spectrum ($Sp_{mes}$) and the estimated stacked spectrum (Emp).

A method according to the invention may use these iterative steps.

Such a device may comprise means of calculating the mean stacking probability using the following formula:

$$P_{mean} = 1 - \left(1 - 2 \times \frac{T_{mort}}{T_{expo}}\right)^{\sum_{j=1}^{N_{max}} Sp_{cor(n-1)}(j)}$$

or the formula:

$$P_{mean} = 1 - \left(1 - 2 \times \frac{T_{mort}}{T_{expo}}\right)^{\sum_{j=1}^{N_{max}} Sp_{cor(n-1)}(j)-1}$$

where $SP_{cor(n-1)}(j)$ is the value of the previously corrected spectrum $SP_{cor(n-1)}$ for channel j, or the measured spectrum if there is no previously corrected spectrum.

A method according to the invention can use this step to calculate the mean stacking probability.

The stacked spectrum may be calculated using the following formula:

$$Emp(k) = \frac{1}{2} \times \sum_{i=1}^{Nc} \sum_{j=i}^{Nc} P_{i,j}(k)$$

where:

$$P_{i,j}(k) = 1 - [1 - 2 \times \delta t_{i,j}(k)/T_{expo}]^{Sp_{cor(n-1)}(E_i) \times Sp_{cor(n-1)}(E_j)}$$

In which $\delta_{i,j}(k)$ determines the size of the interval of time differences $\Delta t$ separating two energy interactions $E_i$ and $E_j$, stacking of which gives a detected energy value $E_k$.

A method according to the invention can use this step to calculate the stacked spectrum.

Means may be included to estimate the function $\delta_{i,j}(k)$ using the inverse function of the stacking function, this latter function associating the energy measured as a function of the time difference $\Delta t$ between these two interactions with a pair of energy interactions (Ei, Ej). This stacking function may be obtained by experimental simulation or by assuming that it is a decreasing affine function of the energy.

According to one embodiment, $\delta t_{i,j}(k)$ is independent of k and is equal to the following regardless of the value k $$\delta t_{i,j}(k) = \partial t_{ij} = \frac{E_{k+1} - E_k}{(E_i + E_j - \max(E_i, E_j))/T_{mort}}$$

A method according to the invention can use either of these steps to calculate the function $\delta_{i,j}(k)$.

A device according to the invention may comprise a circuit capable of outputting an analogue voltage pulse for which the amplitude is proportional to a charge detected by the detector and an analogue/digital converter (ADC) that digitises the analogue pulse and outputs a digital signal, characterised in that it includes a processing circuit on the output side of the analogue/digital converter (ADC), comprising:
  a unit to read digital signals output by the analogue/digital converter (ADC) at a read frequency $f_L$,
  a calculation unit that calculates a time variation (S'(t)) of digital signals read, and
  a circuit capable of capturing digital signals read for which the time variation reaches a predetermined threshold (S1).

In such a device, the processing circuit may also comprise means capable of determining a duration between two successive instants during which the time variation S'(t) reaches a predetermined threshold (S2), where the sign of S2 is opposite to the sign of S1 and means of comparing said duration with a threshold duration value ($T_m$), the means of comparing said duration affecting the capture of the digital pulse read such that a digital pulse read is captured if said determined duration is also less than or equal to the value of the duration threshold.

The means to determine a duration between two successive instants during which the time variation S'(t) reaches a predetermined threshold (S2) may also comprise a counter that is incremented for each determined digital value of S'(t), the count being interrupted as soon as a digital signal S(t) is such that the time variation S'(t) has an amplitude less than the amplitude threshold (S2).

The value of the duration threshold ($T_m$) is preferably the rise time of a signal at the output from a charge preamplifier placed at the input to the device comprising a circuit capable of outputting a voltage pulse with an amplitude proportional to a charge detected by the detector.

The circuit capable of outputting a voltage pulse with an amplitude proportional to a charge detected by the detector preferably comprises a delay line energy measurement circuit.

A method or a device according to the invention using a single detector and a spectrometry technique, in other words the use of an amplitude distribution of pulses measured by the detector, rather than counting techniques.

BRIEF DESCRIPTION OF THE DRAWINGS

FIGS. 23A and 23B show electrical signals characteristic of the circuit in FIG. 18 that show the processing of coincidences and dead times used in the device according to the invention.

DETAILED PRESENTATION OF EMBODIMENTS OF THE INVENTION

Figure 1A:
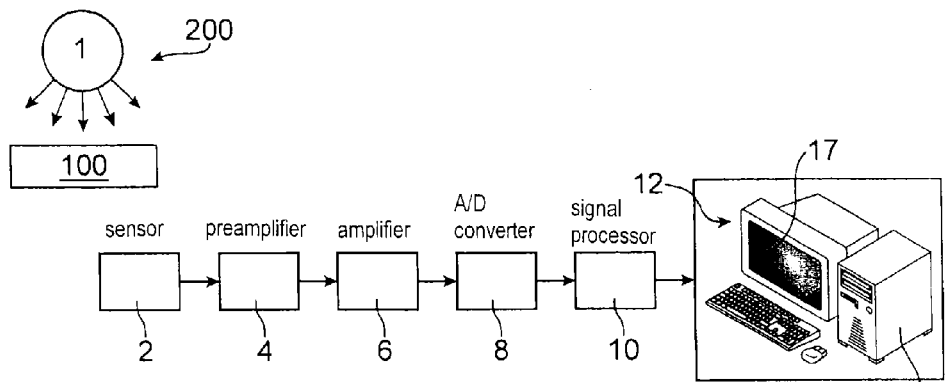
FIGS. 1A and 1B show examples of the device according to the invention.

An example embodiment of a device according to the invention will be given with reference to FIG. 1A. This device is a spectrometry system 1 and comprises the following elements:

- a radiation source 1, that emits radiation 200, for example with a minimum flux of incident photons between $10^6$ mm$^{-2}$s$^{-1}$ and $10^7$ mm$^{-2}$s$^{-1}$
- a sensor 2, for example a direct conversion sensor, for example made of semiconducting material such as CdTe or CdTe:Cl, or CdTe:In or CdZnTe; this sensor is provided with two electrodes at the terminals of which a signal translates an interaction between radiation or a photon and the sensor material, and creation of a cloud of electronic charges in the material of the sensor generated by this interaction. This sensor may for example be parallelepiped in shape comprising two electrodes on two opposite faces, the electrodes for example being arranged to be perpendicular to the incident radiation.

Another type of sensor that could be used is a scintillation type sensor or ionisation chamber, in general any type of sensor that is capable of outputting a signal with an amplitude proportional to the energy deposited by an interaction, the preferred detectors being semiconductors and particularly semiconductors operating at ambient temperature, for example CdTe, CdZnTe, CdMnTe, HgI2, AsGa, Si, TlBr, etc.

One advantage of such a sensor connected to an electronic spectrometry circuit is the possibility of acquiring signals corresponding to well defined energy ranges. The device also comprises:

- a charge preamplifier 4,
- an amplifier 6,
- an Analogue/Digital converter 8,
- means 10 of processing the signal that has been shaped and digitised by means 4, 6 and 8, and forming a radiation spectrum. Other processing means, for example based on delay line circuits particularly to enable shaping of the signal, can be provided on the input side of the analogue digital converter.
- means 12 of spectrum processing using a method conforming with the invention.

A radiation spectrum is a histogram of the amplitude of detected pulses comprising at least two channels, each channel corresponding to a well determined amplitude range. Since the amplitude of a pulse is proportional to the energy deposited in the detector by an interaction, such a spectrum is also a histogram of the energy of detected interactions.

The number of channels is equal to Nc, such that Nc≥2. Each channel comprises pulses with an energy of between Ei and Ei+ΔEi. ΔEi may be identical for each channel such that ΔEi=ΔE for all channels i, and ΔE is then a constant.

When a device is being used, a material sample 100 is placed between the source and the detector so that it can be characterised. This material sample may also be called the examined material.

The means 12 in particular comprise a computer or a microcomputer or a computer programmed to store and process spectra data and data to use a method according to the invention, for example transmitted spectra data I and $I_0$ and/or coefficient data μ(E) or the thickness of the material passed through. Transmission coefficients $α_1$ and $α_2$ described later can thus be calculated.

More precisely, a central processing unit 16 is programmed to implement a processing method according to the invention, using data as a function of the transmission starting from the transmitted spectra data I and $I_0$.

These means 12 may also control the X radiation source 1, to trigger radiation emission and to make one or several measurements using the detector 2.

These electronic means 12 can be used to make a synchronous check that the radiation source(s) and the detector (s) are triggered.

Figure 7:
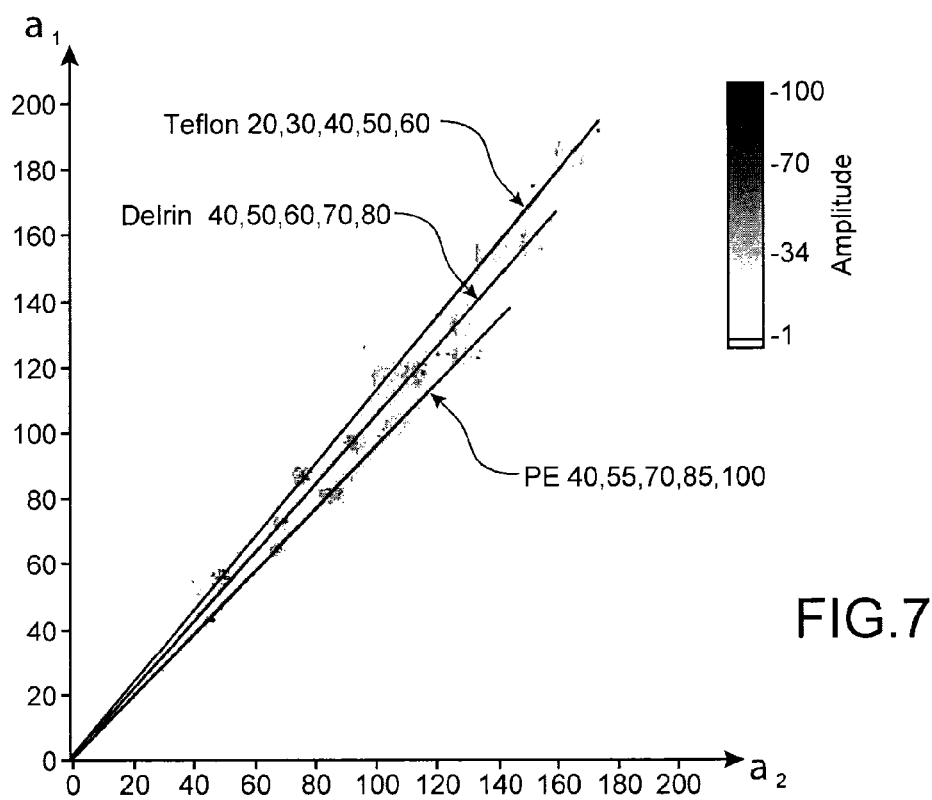
FIG. 7 shows a set of straight lines in a ($\alpha_1$, $\alpha_2$) plane for various materials.

These means 12 can also be used to position estimated coefficients $α_1$ and $α_2$ in a plane like that in FIG. 7 and to deduce the nature of the examined material.

An operator can use the means 12 to select one or several parameters to perform these operations.

In particular, he can select a number N of energy bands, where N≥2, starting from which the transmission coefficients $α_n$, n≥2, can be calculated. Each transmission coefficient is calculated by applying a statistical magnitude to the transmission function within a given energy band. For example, this indicator may be the integral or the mean of the transmission function in the energy band considered.

When N=2, these energy bands correspond to a so-called low energy zone and a so-called high energy zone, and a first transmission coefficient $α_1$ is determined corresponding to the low energy band, and a second transmission coefficient $α_2$ is determined corresponding to the high energy band.

Figure 6:
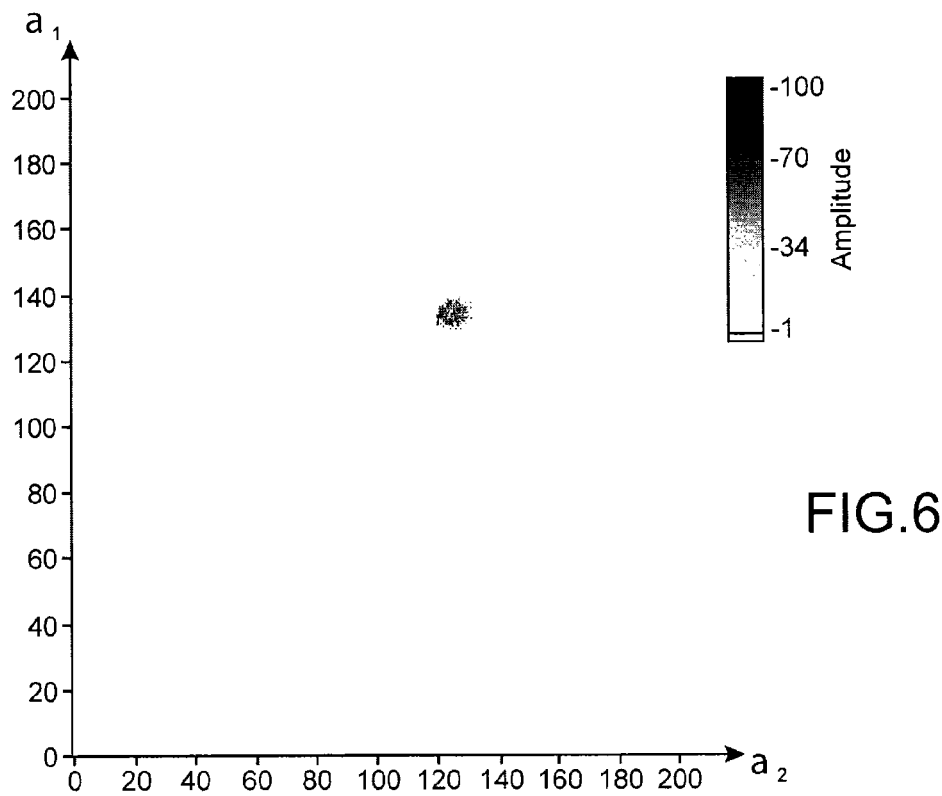
FIG. 6 shows the positioning of a set of measurements in a plane ($\alpha_1$, $\alpha_2$)

Measured spectra I and $I_0$ and one or several transmission functions and/or a representation as shown in FIGS. 6 and 7, can be displayed on the screen or on display means 17. An operator can also use these display means to define or select low energy and high energy zones that will be used to calculate the coefficients mentioned above.

Such a device can also use a delay line that will put pulses into a trapezium shape, coupled with digital electronics and associated processing, for example a circuit for processing and digitisation of an energy spectrum like that described in document EP 2 071 722. Spectrometric measurements can thus be obtained on 256 channels within a measurement time of a few ms.

Figure 1B:
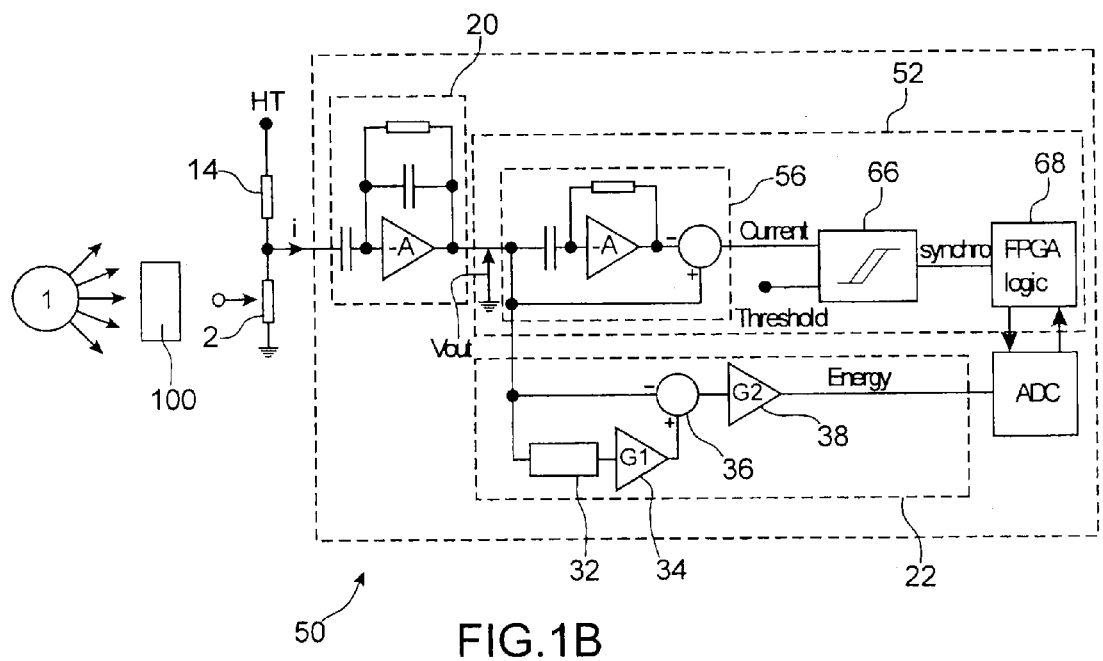

This device shown in FIG. 1B comprises mainly:

- an integrator type charge pre-amplification circuit 20 that can be connected to the semiconductor detector 2 (the resistance 14 denotes a polarisation resistance associated with the detector 2),
- a delay line energy measurement circuit 22 (comprising a delay line 32, a first gain 34, a subtractor 36 and a second gain 38), connected at the output from the pre-amplification circuit, and
- a sampler connected to the output from the energy measurement circuit.

It also comprises a synchronisation circuit 52 comprising:
- a current pulse measurement circuit 56, connected to the output from the pre-amplification circuit 20 and taking the difference between the output and a derivative of the output of the pre-amplification circuit, and a discrimination circuit 66 forming a binary signal as a function of the output from the pulse measurement circuit 22, said logical circuit controlling sampling times of the sampler.

In this figure, references 1 and 100 have the same meaning as in FIG. 1A.

Means such as the means 12 described above may be combined with this circuit to make a device implementing a method according to the invention.

Other aspects of this circuit are described in document EP 2071722.

Furthermore, it would be preferable to use the circuit described below with reference to FIGS. 15-23B. Once again, means like the means 12 described above may be combined with this circuit to make a device implementing a method according to the invention.

The circuit described in FR 09 56844 or in FR 09 58506 may also be used.

A device according to the invention can be used to make a measurement of a spectrum $I_0$ of an incident beam: this spectrum can be averaged over a large number of acquisitions in order to minimise the effect of photonic noise. This spectrum $I_0$ is the radiation spectrum detected by the detector when there is no material (examined material or standard material) between the source and the detector.

The object 100 to be analysed is then positioned in front of the beam (FIG. 1A, typically luggage or more generally a sample of material to be analysed) and the spectrum I of the radiation transmitted through this object for the chosen period is measured, for example between a few hundred µs and a few 100 ms, and generally less than 10 ms or a few tens of ms. This spectrum I may or may not be averaged, but preferably is not.

Figure 2:
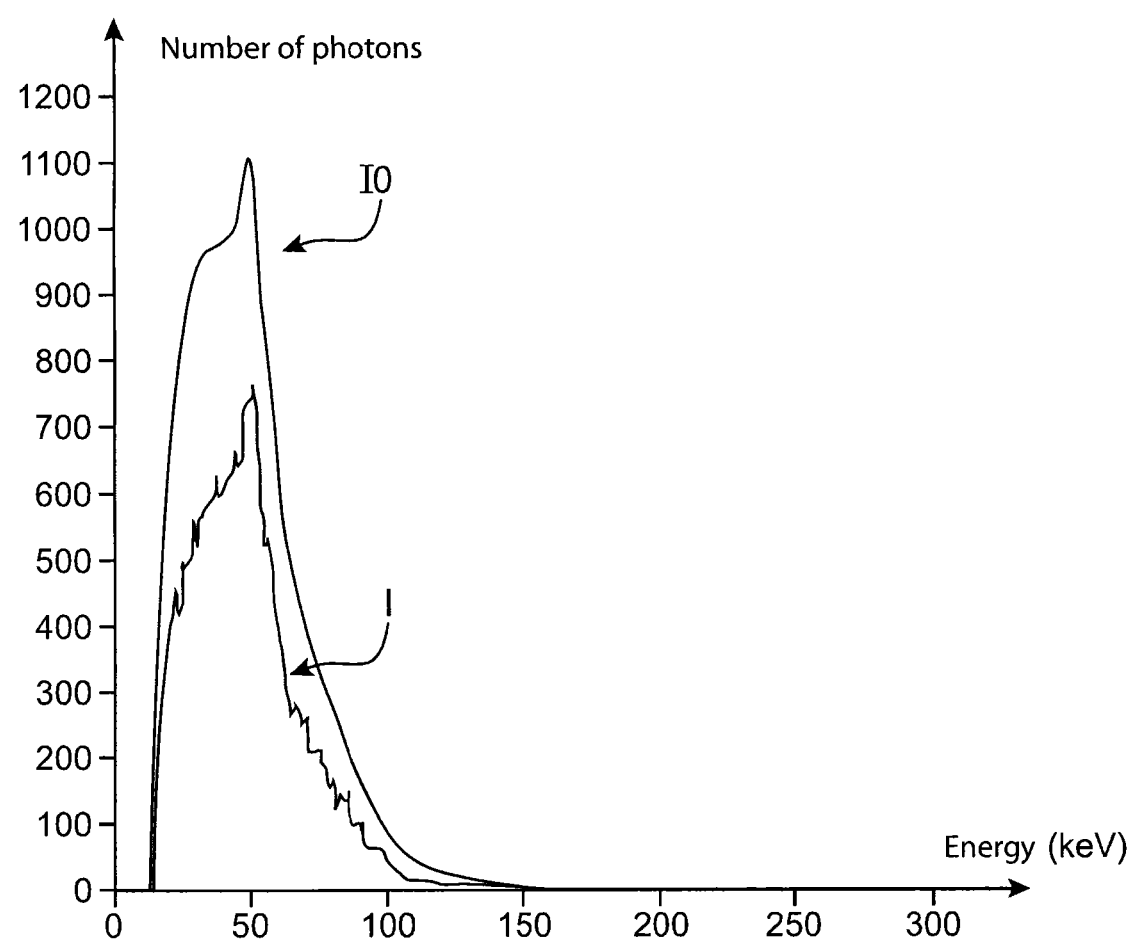
FIG. 2 shows an example of spectra of an incident beam before and after transmission through a material.

An example of the measurements thus made is shown in FIG. 2, which shows the two spectra I and $I_0$.

In general, a transmission function is a function that compares the intensity of radiation transmitted through the object with the intensity of radiation incident to the object, for a given energy or over a given energy range.

Preferably, this comparison is made by a ratio, such that the transmission function is obtained by taking the ratio between the intensity of radiation transmitted through the object and the intensity of radiation incident to this object, at a given energy.

Thus, if $I_0(E)$ denotes the number of incident photons per unit time with energy E, and if I denotes the number of photons transmitted through the object per unit time with energy E, the transmission function can be obtained from $I(E)$ and $I_0(E)$, by taking the ratio between them.

The transmission function TR(E) is then equal to $$TR(E) = \frac{I(E)}{I_0(E)}$$

If µ(E) denotes the linear attenuation coefficient of the material from which the object is made with energy E and if l denotes the thickness of the object through which radiation passes, it is known that $$I(E) = I_0(E) e^{-\mu(E)l}$$

Furthermore, in order to obtain a linearly dependent function of the linear attenuation coefficient of the material from which the object is made, it may be advantageous to express the transmission of photons in the material using the logarithm of the previously described ratio. In this case, the transmission function is equal to $$TR(E) = -\ln\left(\frac{I(E)}{I_0(E)}\right)$$

This function is usually referred to as the attenuation function.

Consequently in this application, the term transmission function refers to:

a function obtained from a ratio between the intensity of the radiation transmitted through the object and the intensity of the radiation incident to the object at a given energy, for example $$TR(E) = \frac{I(E)}{I_0(E)},$$

or a function obtained from the logarithm of the ratio described in the previous paragraph, for example $$TR(E) = -\ln\left(\frac{I(E)}{I_0(E)}\right),$$

this function also possibly being referred to as the attenuation function. This is the definition that will be used throughout the remainder of this application.

Note that I and $I_0$ denote the intensity of the radiation transmitted through the object and the intensity of the radiation incident to the object, respectively. In general I and $I_0$ are fluxes (number of photons per second), but they can naturally also be fluence rates (number of photons per second per unit area) or a number of photons detected during a determined time.

I and $I_0$ are homogenous; they denote the same type of magnitude. I is measured by the detector in the presence of the object between the material and the source, $I_0$ being measured either in the absence of material, or determined by calculation knowing emission parameters of the source.

In the remainder of the description, I and $I_0$ are the number of photons transmitted through the object per unit time and the number of photons incident to the object per unit time, respectively.

For a given material with a given linear attenuation coefficient µ(E) at a given energy E, the Naperian logarithm of the transmission function varies linearly with the thickness of the material.

Figure 3:
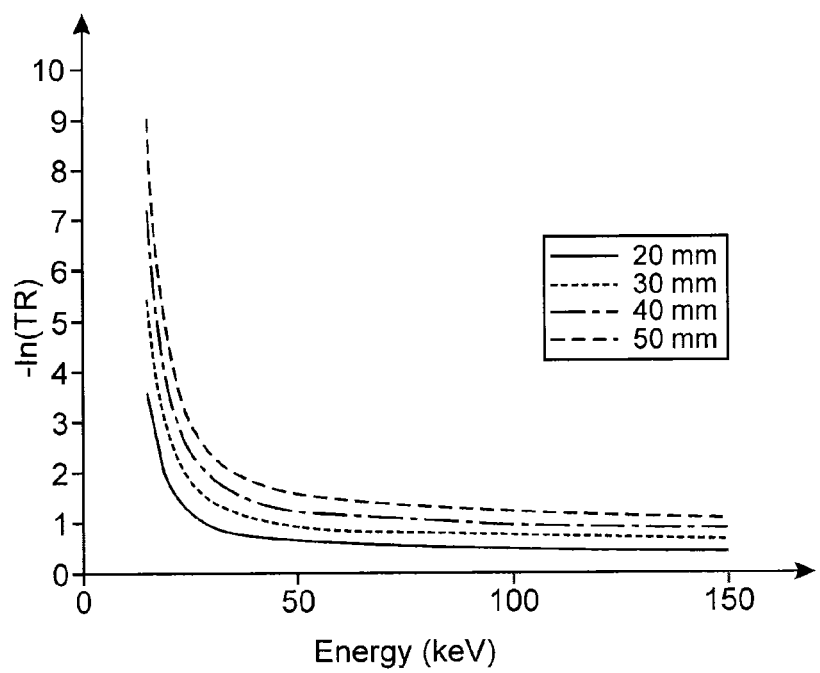
FIGS. 3 and 4 are examples of transmission functions.

FIG. 3 shows transmission functions for a single material (Delrin) with different thicknesses (20 mm, 30 mm, 40 mm, 50 mm). It can be seen that the different transmission functions are proportional to each other.

Figure 4:
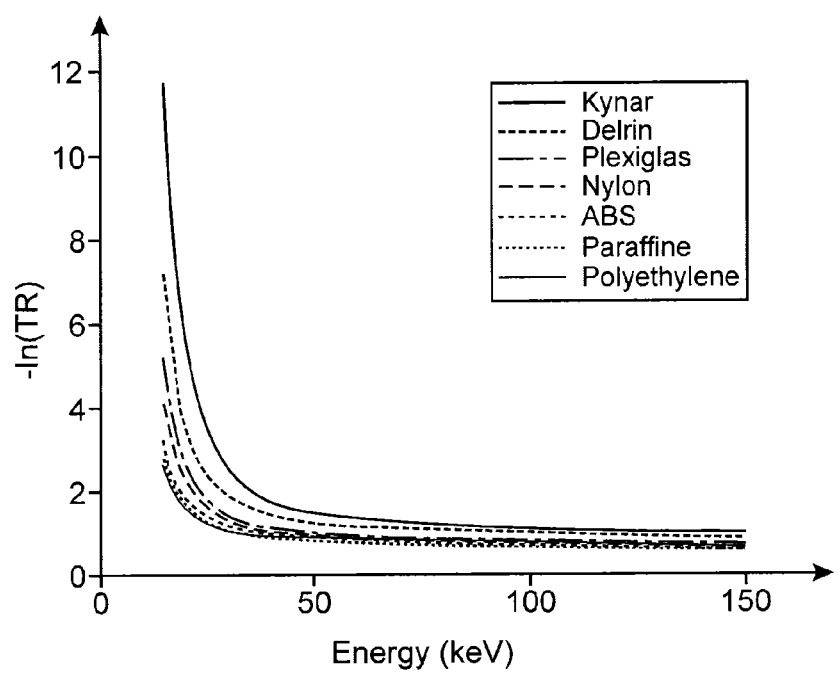

FIG. 4 shows the transmission functions of different materials with the same thickness (40 mm) to determine the energy range in which transmission functions can best discriminate two different materials (in other words materials with different nature).

In this figure, it can be seen that these functions all have the same general shape, but they can differentiate between materials depending on the nature of these materials. They are proportional to each other in high energy ranges (more than 70 keV), while their shapes are better differentiated at low energies (less than 70 keV or even 50 keV).

Consequently, the analysis of the transmission function is a means of characterising an object.

This function forms a signature of the object, signature of its thickness by its multiplication factor relative to a reference thickness and signature of its material that determines the shape of this curve.

Figure 5A:
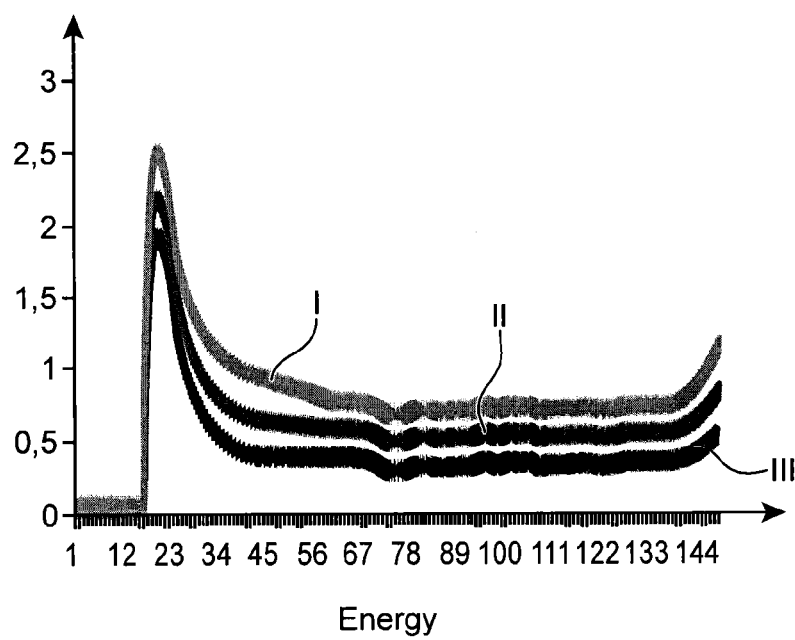
FIGS. 5A-5B show transmission functions averaged over several measurements, low energy and high energy selection zones being shown in FIG. 5B.

An average of the results obtained on a number of measurements can be made which can reduce photonic noise. Thus, FIG. 5A shows an average made on 100 measurements for three plastic materials with different densities, specifically Teflon (curve I), Delrin (curve II) and polyethylene (curve III).

The advantage of Delrin is that its characteristics (density and atomic number) are similar to the characteristics of frequently used explosives.

Figure 5B:
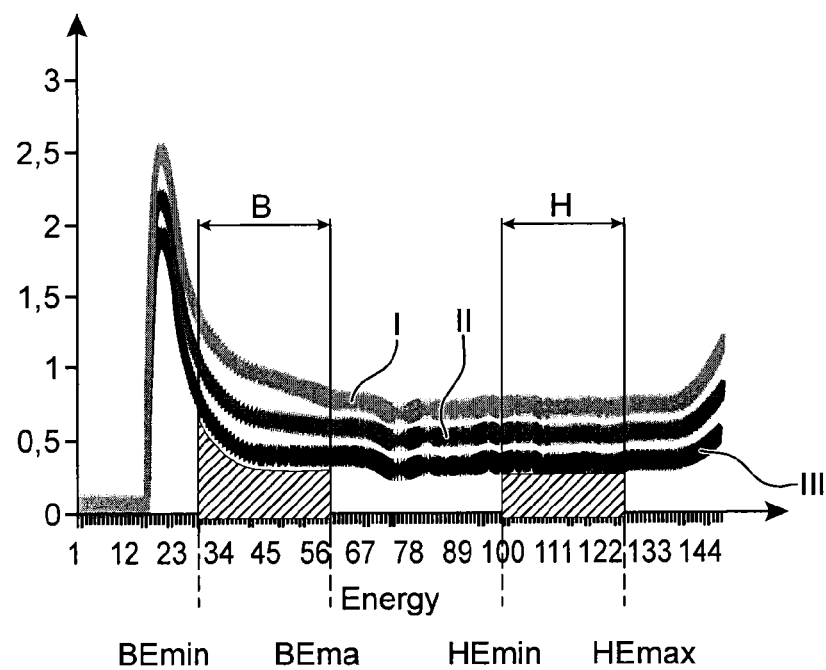

According to one embodiment, two energy bands (N=2) can be considered with a first so-called low energy band (limited by the two values $BE_{min}$ and $BE_{max}$, see FIG. 5B), and a second so-called high energy band (limited by the two values $HE_{min}$ and $HE_{max}$).

More precisely, these two zones can be identified by one or both of the following criteria. Each of these zones is relatively wide, with a width of between 5 keV and 50 keV, and preferably 15-50 keV. A first particularly relevant zone called the low energy zone is between 22 and 40 keV, and a second so-called high energy zone may be chosen at between 50 and 120 keV, and very advantageously between 54 and 112 keV.

Preferably, not each zone has electronic noise type disturbances (affecting low energies). In particular, zones with excessively low statistics will be avoided, particularly at high energies.

Preferably, these zones are limited to channels for which the transmission function has no obvious distortion, thus avoiding extreme channels of the spectrum.

Also preferably, in a first zone, the transmission functions behave significantly differently from each other (low energy), while in the second zone, the transmission functions are relatively parallel to each other (this is the case at high energy). Thus, a first zone will be very sensitive, in other words will vary significantly depending on the nature of the material and/or depending on its thickness, while a second zone will change much less than the first zone as a function of the nature of the material and/or its thickness.

The integral of the transmission curve with respect to the energy variable can be calculated in each of these two zones. But statistical magnitudes other than the integral can also be used, for example the average value.

In the case in which the integral is chosen as the statistical magnitude, the two coefficients are then calculated, each equal to the integral of the transmission function with respect to energy in each of these two zones.

For example for polyethylene, for which the transmission function is denoted $TR_{PE200}(E)$:

$$\alpha 1 = \int_{BE_{min}}^{BE_{max}} TR_{PE200}(E)$$

and $$\alpha 2 = \int_{HE_{min}}^{HE_{max}} TR_{PE200}(E)$$

The same coefficients can be calculated, for example for Teflon and Delrin, and compared with each other for identification.

The two coefficients α1 and α2 are calculated from the transmission function, and this can be made in a short integration time (a few ms).

If a point with coordinates (α1,α2) is represented in a plane for each measurement corresponding to an integration time, the result obtained for example for 1000 successive measurements is a cluster of points with identical or very similar coordinates, as shown in FIG. 6.

The results obtained for several thicknesses of characteristic materials are shown in FIG. 7, always in the (α1,α2) plane, to demonstrate the performances of this method of analysing material transmission functions in order to identify the nature and thickness of these materials.

For a single material, clusters of points (there is one measurement for each point) are aligned on straight line I for Teflon, line II for Delrin and line III for polyethylene.

The variation in thickness (expressed in mm) makes this cluster move along the straight line that applies to it. This cluster corresponds to all points with coordinates $(\alpha_1, \alpha_2)$ for a single material and for different thicknesses. This cluster or this set of points can be determined by interpolating different measurements in order to calculate the coefficients $(\alpha_1, \alpha_2)$ corresponding to different thicknesses, for a single material.

The result is that different standard materials can be used, and a set of standard points can be determined for each standard material, each set of standard points being determined from standard points ($\alpha_{standardmaterial1}$, $\alpha_{standardmaterial2}$) corresponding to different thicknesses of a single standard material. A standard point with coordinates ($\alpha_{standardmaterial1}$, $\alpha_{standardmaterial2}$) may be obtained by measurement or by interpolation of several measurements made with different thicknesses of a single standard material.

Consequently, the two coefficients (α1,α2) can be used to determine the nature and/or thickness of an examined material. This positioning operation in the (α1,α2) plane can be done automatically using means 12. For example, the set of standard points closest to the point with coordinate (α1,α2) can be determined. This can determine the nature of the examined material. If it is also required to determine the thickness of such a material, the closest standard point can be determined, the thickness of the examined material then being considered to be equal to the thickness corresponding to the closest standard point ($\alpha_{standardmaterial1}$, $\alpha_{standardmaterial2}$).

In a method according to the invention, a measurement (or estimate) of $I_0$ and I is made, as described above.

The system then calculates in real time the transmission function TR(E) for each energy channel, that can be expressed by $$-\ln\left(\frac{I}{I_0}\right) = \mu(E) \cdot l$$

The result is thus the transmission function corresponding to the material through which the beam passes as a function of the energy, as shown in FIG. 4.

The next step is to choose the B, H bands, for example, using means 12, 16 and 17, and then to calculate the two coefficients $\alpha_1$, $\alpha_2$. It is then possible to determine the nature and thickness of the observed materials, as explained above with reference to FIG. 7.

The data in FIG. 7 can be stored in a data processing device.

The two coefficients $\alpha_1$, $\alpha_2$ can also be positioned in the plane in FIG. 7 by such a device. In other words, the entire method can be automated.

In general, it can be understood that the natures and/or thicknesses of the measured materials are determined by comparing the values of the measured transmission coefficients ($\alpha 1$, $\alpha 2$) with one or several pairs of standard transmission coefficients ($\alpha 1_{standardmaterial}$, $\alpha 2_{standardmaterial}$), the pairs of standard transmission coefficients ($\alpha 1_{standardmaterial}$, $\alpha 2_{standardmaterial}$) being obtained from transmission functions corresponding to one or several standard materials with known nature and thickness, for the same energy bands.

Up to now, we have described an embodiment according to which a distinction is made between two energy bands of the transmission function TR(E), each band being used to define a transmission coefficient $\alpha i$ $1 \le i \le 2$. But this invention can be generalised to the determination of N transmission coefficients $\alpha i$, $1 \le i \le N$ and N possibly being >2, each coefficient $\alpha i$ being determined from a statistical magnitude, for example the integral, applied to a spectrum energy band of the transmission function with respect to energy.

This measurement can then be represented in a space with N dimensions, each axis in this space then representing the values of a transmission coefficient $\alpha_i$. Thus, there is a point in this space with N dimensions corresponding to each measurement, the coordinates being equal to $(\alpha_1, \alpha_2, \ldots \alpha_N)$ Each Nuplet of transmission coefficients ($\alpha 1, \alpha 2, \ldots \alpha N$) determined with an unknown material can be compared with one or several Nuplets of standard transmission coefficients ($\alpha_{istandardmaterial}$, $\alpha_{Nstandardmaterial}$) obtained with one or several standard materials with known natures and thicknesses.

Each Nuplet of standard transmission coefficients or standard Nuplet is obtained determining the transmission function TR(E) with a standard material with a known nature and thickness. In other words, for each standard material, a transmission function is produced, N energy bands are selected and an indicator $\alpha i$ is produced at each of these energy bands. Naturally, it will be understood that preferably the energy bands and statistical magnitudes used to determine the transmission coefficients of the examined material ($\alpha 1, \alpha 2, \ldots \alpha N$) and the standard transmission coefficients ($\alpha_{istandardmaterial}, \ldots \alpha_{Nstandardmaterial}$) are the same.

It is also possible to determine a standard Nuplet for a standard material with a given nature and thickness, by interpolating several standard Nuplets corresponding to a material with the same nature but different thicknesses.

It would also be possible to define a set of standard points for each standard material, each set including standard Nuplets corresponding to the same standard material. Depending on the value of the N, this set might be in the form of a straight line (for example for N=2), or a 3D surface (for example for N=3).

When the transmission coefficient Nuplet ($\alpha 1, \alpha 2, \ldots \alpha N$) corresponding to an unknown material has been determined, the nature and thickness of said unknown material can be obtained by comparing this Nuplet ($\alpha 1, \alpha 2, \ldots \alpha N$) with different standard Nuplets.

Each Nuplet of an examined material ($\alpha 1, \alpha 2, \ldots \alpha N$) may be compared with one or several standard Nuplets ($\alpha_{istandardmaterial}, \ldots \alpha_N$standardmaterial) for example by making a measurement of the distance between a Nuplet ($\alpha 1, \alpha 2, \ldots \alpha N$) and each standard Nuplet ($\alpha_{istandardmaterial}, \ldots \alpha_N$standardmaterial) of each standard material. The nature and thickness of the examined material then correspond to the nature and thickness of the standard material represented by the standard Nuplet with the closest coordinates.

For example, the Euclid distance could be used.

It would also be possible to determine only the nature of a material. In this case, it will be assumed to be the nature of the standard material corresponding to the closest standard Nuplet or the nature of the closest set of standard points (remember that a set of standard Nuplets corresponds to the group of standard points corresponding to the same standard material).

It would also be possible to determine only the thickness of a material, for example if the nature of this material is assumed to be known. In this case, it will be assumed to be the thickness of the standard material corresponding to the closest standard Nuplet.

An example of the use of a method according to the invention comprises the following steps:
  make a measurement of the energy spectrum of the incident beam,
  position the object 100 to be characterised on the path of the incident beam and measure the spectrum of the transmitted beam
  calculate the transmission function of the object, for example $$-\ln\left(\frac{I}{Io}\right),$$

over the entire energy range and with all channels,
  calculate two transmission coefficients: the first coefficient $\alpha_1$ obtained by summating the transmission function on low energy channels, and the second transmission coefficient $\alpha_2$ obtained by summating the transmission function on high energy channels, the summation intervals preferably being chosen as indicated above, particularly to avoid distortion zones of the transmission function,
  identify the nature and the thickness of the object to be identified, using these two coefficients.

The invention can be used to make fast spectrometry, for example with a duration of the order of or less than a few seconds and under intense radiation, on a large enough number of energy channels to be able to differentiate materials by analysing their transmission functions in the very short times imposed for a fast analysis.

In comparison, the known systems that were mentioned in the introduction, use detectors associated with counters; therefore they are capable of counting photons originating from each detector, but they are not sufficient to select detected photons in one or several determined energy bands. Unlike this invention, they do not make any spectrometric measurements which however could be very useful for identification of materials because they could be used to obtain a transmission function as a function of the energy, starting from a single detector.

When the measurements have to be made quickly, particularly in an application to measurement on luggage, the photonic radiation is intense, the fluence rate usually being between $10^6$ photons/mm$^2$/s and $10^7$ photons mm$^2$/s. For this type of application, the measurement time will be short, usually less than a few tens of ms, or even about 10 ms.

Therefore, a signal processing method could be used in preference capable of detecting and correcting spectra disturbed by stacking phenomena.

Such a method that can be used within the scope of this invention is presented below with reference to FIGS. 8A-14B.

Starting from incident X radiation 200 with a spectrum $Sp_0$, a spectrum $Sp_{mes}$ is measured using the sensor 2 and, for example, processing means 4-12 or the device in FIG. 1B or a device according to one of FIGS. 15-20. Let $T_{expo}$ be the exposure time, namely the time necessary to acquire this spectrum.

Such a spectrum comprises disturbances that originate from photon stacking phenomena.

The number of photons of the incident radiation 200 at a given energy E is denoted $Sp_0(E)$.

Let $P_{mean}$ be the probability for each photon of stacking with at least one other photon.

The spectrum measured at energy E can then be deduced from the incident spectrum by the following equation:

$$Sp_{mes}(E)=Sp_0(E)\times(1-P_{mean})+Emp(E)$$

The factor $(1-P_{mean})\times Sp_0(E)$ represents all photons that have not been stacked.

The term $Emp(E)$ is the contribution to the measurement, at energy E, of all photons in the spectrum $Sp_0$ that are stacked (in other words the "stacked spectrum"). $Emp(E)$ depends on the incident spectrum $Sp_0$ and the behaviour of the system formed by the sensor 2 and by electronic means 4-10 regarding photons detected at very close times, in other words in a stack situation.

The dead time $T_{dead}$ is defined: this is the minimum time separating two interactions (two events), below which only one of the two events is detected.

For two incident photons on the sensor, stacking takes place for a duration $T_{expo}$ if the interaction time $t_1$ of a photon in the sensor 2 is separated in time from the interaction time $t_2$ of the other photon in the sensor 2 by a duration less than $T_{dead}$, in other words if $|t_2-t_1|\leq T_{dead}$. The arrival of photons in the detector 2 is assumed to be equally probable throughout the duration $T_{expo}$, consequently the probability of these two interactions being stacked is equal to:

$$P_0=2\times T_m/T_{expo}$$

Conversely:
the probability that an interaction produced by an incident photon will not be stacked with an interaction produced by another photon is $1-P_0$.
the probability for this same interaction of not being stacked with another interaction of another photon is equal to the product of the probabilities of the different events, because they are independent events.

The probability $P_{mean}$ of an interaction produced by an incident photon stacking with at least one other interaction produced by another photon is therefore equal to:

$$P_{mean}=1-(1-P_0)^{N-1}$$

where N is the number of detected photons, in other words the number of hits measured in the incident spectrum:

$$N = \sum_E Sp_0(E).$$

In the following, since the energies are discretised, the energy range of photons detected without stacking in the $i^{th}$ channel of the spectrometric sensor is denoted $E_i$. The approximation according to which all stacks are two photons stacks exactly is used in order to estimate the stacked spectrum.

The limits of this approximation are studied and discussed later.

When two photons are absorbed by the sensor in a stacking situation, only one event is counted.

Figure 8:
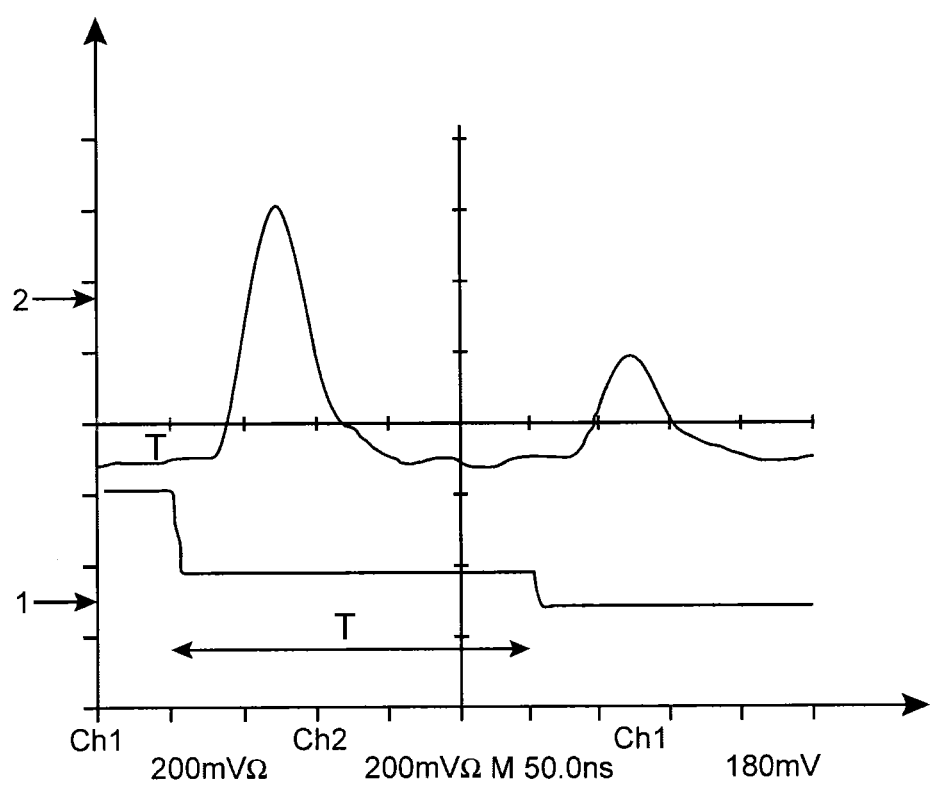
FIG. 8 shows measurements made on an experimental spectrometry system.

In order to get a good understanding of this aspect, FIG. 8 shows measurements made on an experimental spectrometry system, more precisely it shows pulses generated by two particles in time after shaping by the electronic circuit.

Only one interaction is counted for a short time shift (the interaction time $t_1$ of the first photon and the interaction time $t_2$ of the other photon satisfy the inequality $|t_2-t_1|\leq T_{dead}$), while two interactions corresponding to the two photons are counted for a time shift of more than about $T_{dead}$.

Furthermore, when a single interaction is counted, the energy does not correspond to the energy deposited by one of these photons, but rather to a different energy. The stacked spectrum $Emp(E)$ corresponds to an estimate of the part of the measured spectrum $Sp_{mes}(E)$ resulting from stacking. It is obtained by quantifying the energy at which a single event counted for two interactions in a stacking situation is measured. The estimate of this stacked spectrum is made in two steps:

the first step is to model stacking functions with two photons,
these functions are summated over all possible energy pairs $E_i$, $E_j$, where $1\leq i\leq Nc$ and $j\leq i\leq Nc$, Nc being the number of channels to estimate the stacked spectrum.

Let us assume a pair of photons depositing energies ($E_i$, $E_j$) in the detector, to make the initial estimate of stacking functions with two photons, or more precisely with interactions produced by two photons.

The function that associates the energy measured as a function of the shift $\Delta t$ between the arrival times of the two photons with this pair is called the stacking function:

$$F_{E_i,E_j}:\Delta t \mapsto E$$

$$[0,T_{mort}]\rightarrow[\max(E_i,E_j),E_i+E_j]$$

In other words, the stacking function $F_{Ei,Ej}$ creates a relation between the time shift between two stacked interactions with energies Ei and Ej and the energy assigned to this stack.

We will give an example of the method used to model this function, which is a decreasing function of the shift $\Delta t$, later in the description.

This function reaches its maximum value $E_i+E_j$ at $\Delta t=0$. It is then a coincident detection; the two photons that interacted are therefore indissociable and their energies are added.

The minimum value of this function is maximum ($E_i,E_j$). The measured energy always remains greater than or equal to the energy deposited by the photon that deposited the highest energy in the detector, in other words max ($E_i$, $E_j$)

Figure 9:
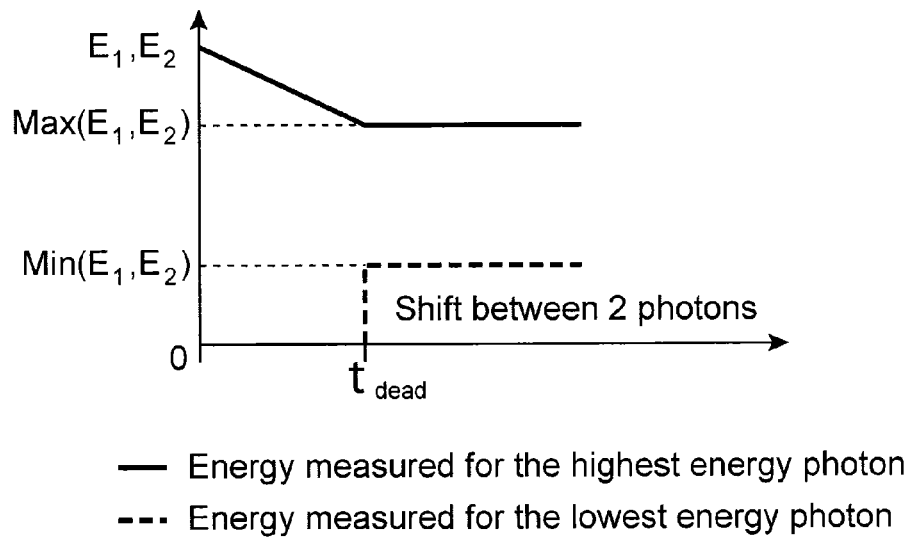
FIG. 9 shows a model stacking function with two photons.

This is shown in FIG. 9, in which the top figure shows the energy measured for the photon with the highest energy max(E1, E2), and the bottom figure shows the energy measured for the photon with the lowest energy min(E1, E2).

For a zero time shift (case of coincident detection), the measurement is distorted because an event is measured with an energy equal to the sum of the energies of the photons (namely $E_1+E_2=\max(E_1,E_2)+\min(E_1,E_2)$).

For a shift greater than or equal to the dead time, each of the two photons is measured at its own energy (with the highest energy photon at max(E1, E2) and the lowest energy photon at min ($E_1$, $E_2$)).

For an intermediate time shift, an event with an energy variable between $E_1+E_2$ is measured. It can be seen that this is a continuous function decreasing over the interval [0, $T_{dead}$].

Therefore this function of the measured energy as a function of the time shift can be inverted. Its inverse denoted $F^{-1}$ is used to associate a time interval with an energy between the maximum value $E_i+E_j$ and the minimum value max($E_i,E_j$), as follows:

$$F^{-1}_{E_i,E_j}: E \mapsto \Delta t$$

$$[\max(E_i,E_j), E_i+E_j] \to [0, T_{mort}]$$

Since the energy range is discretised, this inverse function $F^{-1}_{EiEj}(E_k)$ is determined as follows:

for $E_k$ included within the interval [max($E_i$, $E_j$), $E_i+E_j$], $F^{-1}_{EiEj}(E_k)$ is the time shift between two interactions with energies $E_i$ and $E_j$, a shift which results in a stack with energy $E_k$, for $E_k$ outside the interval [max($E_i$, $E_j$), $E_i+E_j$], $F^{-1}_{EiEj}(E_k)=0$; there is no time shift that could supply such energy because it is outside the possible values.

Considering the significance of the function F given above, this inverse function $F^{-1}_{EiEj}(E_k)$ represents the time difference between two interactions with energies $E_i$ and $E_j$, such that these interactions are considered as being a single interaction with energy $E_k$.

This function $F^{-1}_{EiEj}(E_k)$ can be chosen to be linear.

We can now calculate the elementary stacked spectrum.

We will calculate the spectrum generated by stacks between photons with energy $E_i$ and photons with energy $E_j$.

This is done by discretising the energy interval [max($E_i$, $E_j$), $E_i+E_j$] into energy channels $E_k$ each with the width of a channel of the spectrometric sensor, therefore we have $$\frac{E_i + E_j - \max(E_i, E_j)}{\Delta E}$$

channels, where $\Delta E$ corresponds to the energy range corresponding to each channel, in this case this range being assumed to be identical for each of the Nc channels. For each value of k, the time interval $\delta t_{i,j}(k)$ associated with energy channel $E_k$ is given by the following equation:

$$\delta t_{i,j}(k) = F^{-1}_{EiEj}(E_{k+1}) - F^{-1}_{EiEj}(E_k)$$

The probability that at least one of the photons with energy $E_j$, denoted $Sp_0(E_j)$ will lie within the time interval between $F^{-1}_{EiEj}(E_k)$ and $F^{-1}_{EiEj}(E_{k+1})$ relative to a photon with energy i, can be estimated:

$$P_{i,j}(k) = 1 - [1 - 2 \times \delta t_{i,j}(k)/T_{expo}]^{Sp_0(E_i) \times Sp_0(E_j)}$$

$P_{i,j}(k)$ is the contribution of photons with energy $E_i$ stacked with photons with energy $E_j$, to the energy $E_k$ of the stacking function.

In other words, for each channel (k) corresponding to energy Ek, $P_{i,j}(k)$ represents the probability that an event counted in this channel corresponds to a stack of two interactions separated in time by a duration of less than $T_{dead}$, with corresponding energies $E_i$ and $E_j$. $P_{i,j}$ will be called the stacking probability and there will be as many stacking probabilities $P_{i,j}$ as there are pairs (i,j) with $1 \le i \le Nc$ and $1 \le j \le Nc$ or $i \le j \le Nc$.

The stacked spectrum Emp is then estimated by summating, for each channel k, all or some of the stacking probabilities previously defined for each pair i and j.

This can be done iteratively by a loop on all or some of the pairs ($E_i$, $E_j$). If the number of energy channels of the spectrometric sensor is denoted Nc, the resulting spectrum is the sum of $Nc^2/2+Nc/2$ elementary stacking spectra:

$$Emp(k) = \sum_{i=1}^{Nc} \sum_{j=i}^{Nc} P_{i,j}(k)$$

In practice, the objective is to estimate the dead time $T_{dead}$ and the stacking function with two photons. There are various possible methods for each case.

The dead time $T_{dead}$ can be obtained firstly by:

simulating pulse shapes at the output from the analogue electronics, after absorption of a particle by the semiconductor 2 and then filtering and processing of the signal emitted by the analogue electronics, then estimating the minimum duration between two photons at which they can be separated.

With this first method, the influence of digital processing of pulses on the dead time is neglected.

As a variant, an experimental method is used to analyse the pulse signal experimentally.

According to a first experimental method:

the first step is to read the signal at the output of the means 4, 6 (analogue electronics), before digitisation and construction of the spectra, the next step is to estimate the minimum duration separating two photons at which they can be separated.

According to a second experimental method, spectrum analyses are made:

the first step is to estimate the measured count rate as a function of the incident flux (number of photons/s): different spectra are made at different count rates, making the intensity I of the radiation generator 200 vary. The theoretical count rate is calculated assuming that it is proportional to I. The reference value is estimated for the lowest flux for which it is considered that the stacking phenomenon is negligible (typically a stacking probability for an incident photon of less than 1%), the next step is to choose a model for the system, for example the model known under the name paralysable $$f(n) = n e^{-n \times T_{mort}}$$

or based on the model known under the name non-paralysable:

$$f(n) = \frac{n}{1 - n \times T_{mort}}$$

or any other function considered as being relevant by those skilled in the art.

Where n is the theoretical count rate, in other words the count rate in the lack of any stacking.

The next step is to calculate the dead time, by adjustment of f(n) to experimental count rate data.

Some pulse processing and spectrum formation devices can also be used to determine a dead time. This magnitude can also be considered as being a dead time that can be used by the invention.

Figure 10:
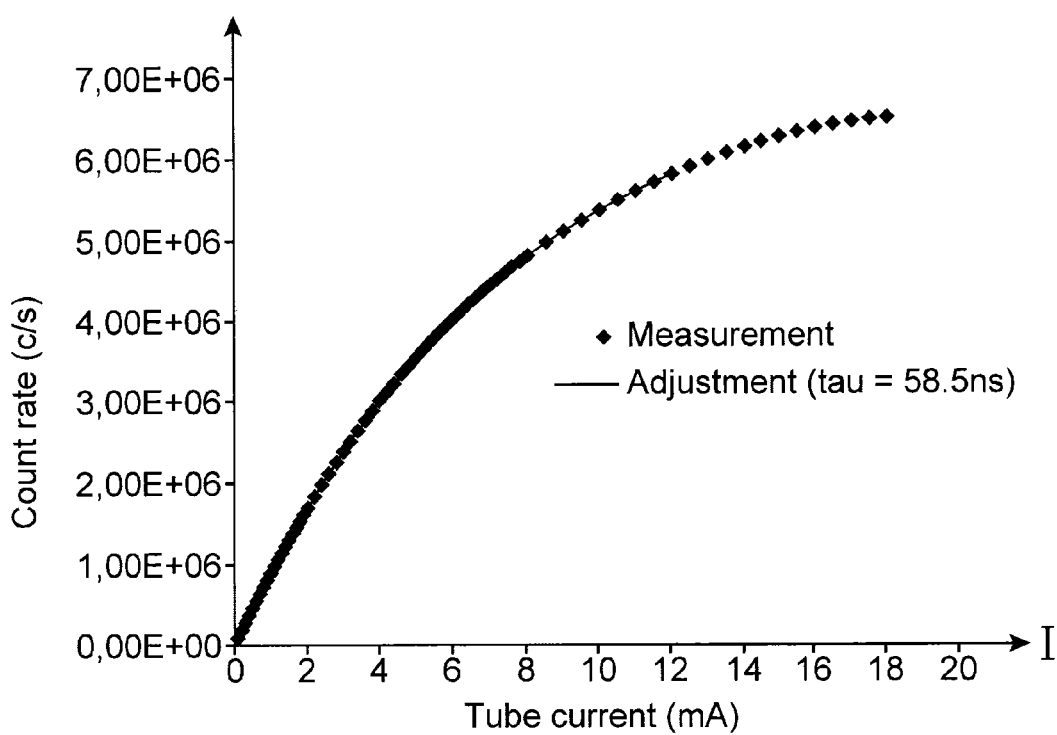
FIG. 10 shows a measurement of the dead time by adjustment of the count rate formula to experimental data for a system that can be paralysed.

FIG. 10 shows this principle, the adjustment then being made according to a paralysable model preferred by the inventors. A set of count measurements (represented by points) is made for different incident flux values adjusted using the current I from the X tube (in mA). The formula for the count rate for a paralysable system is then adjusted onto the experimental data by varying the dead time $T_{dead}$ of the system. The adjustment then gives a dead time of 58 ns.

Concerning the stacking function, an estimate can be made by simulation of output pulse shapes emitted by the semiconductor 2 during absorption of a particle and filtering of this signal by the processing electronics. Then the stacking function is estimated by simulating the response of the system when two pulses are applied to it corresponding to $E_i$ and $E_j$, and varying the time difference $\Delta t$ between these two pulses. The stacking function $F_{EiEj}(\Delta t)$ corresponding to the energy E output from the stack of the two energy pulses $E_i$ and $E_j$ is then estimated as a function of the time difference $\Delta t$ separating these two interactions. Digital processing of the pulses can be neglected. In this case, this simulation can be used to estimate the analogue signal shape corresponding to the input to block 8 in FIG. 1. Otherwise, it can be done experimentally:

- by using a pulse generator at the input to means 4 or 6 forming the preamplifier or the amplifier respectively of the analogue electronics,
- by measuring the energy $E_k$ produced by two generated pulses corresponding to energies $E_i$ and $E_j$, as a function of their time difference $\Delta t$.

Finally, another method is the so-called "affine model". Since the energy measured decreases linearly with the shift between the interaction times of the two photons, it can be assumed that an affine type stacking function with two photons is applicable, which linearly relates the measured energy and the time shift $\Delta t$. The validity of this model was verified during an experimental study not described herein:

$$F_{E_i,E_j}:\Delta t \mapsto \max(E_i,E_j) - \Delta t \times (E_i+E_j-\max(E_i,E_j))/T_{mort}$$
$$[0,T_{mort}] \to [\max(E_i,E_j),E_i+E_j]$$

The inverse of the stacking function with two photons that associates a time interval separating the two photons with an energy, denoted $F^{-1}_{EiEj}$, is then deduced using the following formula:

$$F^{-1}_{E_i,E_j}:E \mapsto \frac{E - \max(E_i, E_j)}{(E_i + E_j - \max(E_i, E_j))/T_{mort}}$$
$$[\max(E_i, E_j), E_i + E_j] \to [0, T_{mort}]$$

Thus, for E(k) such that $\max(E_i, E_j) \leq E(k) \leq E_i+E_j$, $F^{-1}_{EiEj}(E_k)$ corresponds to the time shift of the two interactions $E_i$ and $E_j$.

For an energy E(k) such that $E(k) < \max(E_i, E_j)$ or $E(k) > E_i+E_j$, $F^{-1}_{EiEj}$ is not defined.

We have already seen that the time interval associated with the energy channel $E_k$ is given by the following equation:

$$\delta t_{i,j}(k) = F_{EiEj}^{-1}(E_{k+1}) - F_{EiEj}^{-1}(E_k)$$

According to the assumption of an affine function F:

$$\delta t_{i,j}(k) = \frac{E_{k+1} - E_k}{(E_i + E_j - \max(E_i, E_j))/T_{mort}} \quad (1)$$

If the energy range $\Delta E_k$ for each channel k is constant and equal to $\Delta E$, $$\delta t_{i,j}(k) = \frac{\Delta E}{(E_i + E_j - \max(E_i, E_j))/T_{mort}}$$

and is therefore a constant for given i and j; in other words according to this assumption, $\Delta t_{i,j}(k)$ only depends on i and j regardless of the value of k.

The function $\delta t_{i,j}(k)$ determines the size of the interval of time differences $\Delta t$ separating two energy interactions $E_i$ and $E_j$, the stack of which gives a detected energy value $E_k$. When the time difference $\Delta t$ between these two interactions is such that:

$$F^{-1}_{EiEj}(k) \leq \Delta t < F^{-1}_{EiEj}(k) + \delta t_{i,j}(k),$$

the stack leads to a detected energy equal to $E_k$.

If the time difference $\Delta t$ is not within the time interval defined by the previous equation, for example if $$F^{-1}_{EiEj}(k) + \delta t_{i,j}(k) \leq \Delta t < F^{-1}_{EiEj}(k) + \delta t_{i,j}(k) + \delta t_{i,j}(k+1),$$

which can be written $$F^{-1}_{EiEj}(k+1) \leq \Delta t < F^{-1}_{EiEj}(k+1) + \delta t_{i,j}(k+1)$$

then the stack leads to a detected energy equal to $E_{k+1}$.

Therefore, it can be seen that there is an interval with width $\delta t_{i,j}(k)$ delimiting the time differences $\Delta t$, such that two interactions with energies $E_i$ and $E_j$ separated in time by a difference $\Delta t$ included in this interval, are stacked and considered as being a single interaction with energy $E_k$. $\delta t_{i,j}(k)$ could also refer to the width of a window containing the time differences $\Delta t$, such that two interactions with energy $E_i$ and $E_j$ separated in time by such differences are considered as a single stack with energy $E_k$.

Figure 11:
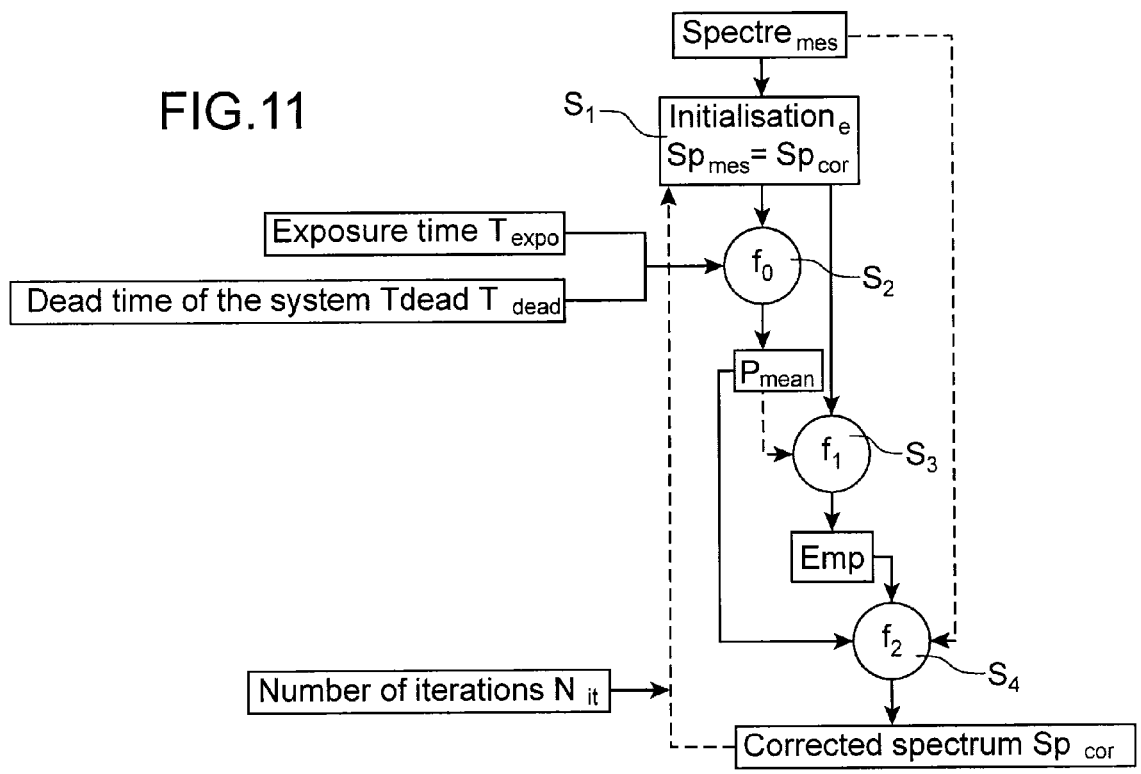
FIG. 11 shows the embodiment of an iterative method according to the invention.

A correction method according to the invention that uses the ($T_{dead}$, Emp, stacking function) elements will now be explained with reference to FIG. 11.

This method can be used to deduce a corrected spectrum $Sp_{cor}$ from a spectrum measurement $SP_{mes}$ degraded by the stacking phenomenon.

But the incident spectrum $Sp_0$ is usually unknown, and it is then impossible to estimate the stacking probability $P_{mean}$, the stacking probabilities $P_{i,j}$ or the stacked spectrum Emp based on the previously described expressions. The correction of stacks is then based on an iterative estimate of the mean stacking probability $P_{mean}$/the stacking probabilities Pi,j and the stacked spectrum Emp, for example using the following expressions $P_{mean} = 1 - (P_0)^{N-1}$ where $$N = \sum_E Sp_{cor}(E)$$

$$P_{i,j}(k) = 1 - [1 - 2 \times \delta t_{i,j}(k)/T_{expo}]^{Sp_{cor}(E_i) \times Sp_{cor}(E_j)}$$

and $$Emp(k) = \sum_{i=1}^{Nc} \sum_{j=i}^{Nc} P_{i,j}(k)$$

If the correction method is iterative, $Sp_{cor}$ will be considered to be established starting from the measured spectrum $Sp_{mes}$ during the first iteration; but for subsequent iterations, a corrected spectrum $Sp_{cor(n)}$ will be produced from the corrected spectrum $Sp_{cor(n-1)}$ obtained during the previous iteration (One assumes $1 \leq n \leq N_{it}$, where $N_{it}$ is the number of iterations). For example, the spectrum $Sp_{cor}$ may be equal to the spectrum $Sp_{mes}$ during the first iteration, and during successive iterations $Sp_{cor}$ may be equal to the spectrum corrected during the previous iteration.

If there is only a single iteration, $Sp_{cor}$ is established starting from the measured spectrum $SP_{mes}$, for example $Sp_{cor}=Sp_{mes}$.

This method comprises 4 input variables:
the spectrum to be corrected $Sp_{mes}(j)$, that is actually a column vector with its dimension equal to the Number of channels ($N_C$)×1.

This spectrum (digitised) was obtained by measurement, for example using the device in FIG. 1A or 1B or one of the FIGS. 15-20.

The integration time $T_{expo}$. This is a real number given in ms, and this is a physical data of the system depending on the radiation source used.

The dead time of the electronic sensor system $T_{dead}$. This is a real number given in ms. We have explained how it can be measured or estimated.

The number of iterations for correction of stacks, therefore made iteratively, $N_{it}$. This number may for example be chosen by an operator of the data processing system. This number is not necessarily predetermined. The method will then be stopped by the operator or based on a convergence criterion, by comparing two spectra corrected during the two successive iterations.

The method provides a corrected stacked spectrum, $Sp_{cor}$ at the output, and also a vector with dimension $N_C$×1.

This method comprises firstly (step S1) initialisation of the spectrum corrected from the measured spectrum, for example $Sp_{cor(0)}=Sp_{mes}$. In other words during initialisation, the measured spectrum is identified with the corrected spectrum.

According to one embodiment, an iterative correction is then done $N_{it}$ times. The following steps are carried out during each iteration:
a calculation of the mean stacking probability (function $f_0$) (step S2),
an estimate of the stacked spectrum (function $f_1$) (step S3),
a correction of stacks (function $f_2$) (step S4) to provide a corrected spectrum $Sp_{cor}$.

Step S2 starts from three input parameters $SP_{cor(n-1)}$ (which is a vector initialised as mentioned above); $T_{dead}$ (real number); $T_{expo}$ (real number), to provide a real number P by making a single step calculation:

$$P_{mean} = 1 - \left(1 - 2 \times \frac{T_{mort}}{T_{expo}}\right)^{\sum_{j=1}^{N_C} Sp_{cor}(j)}$$

or more rigorously:

$$P_{mean} = 1 - \left(1 - 2 \times \frac{T_{mort}}{T_{expo}}\right)^{\sum_{j=1}^{N_C} Sp_{cor}(j)-1}$$

Starting from the two parameters, specifically $Sp_{cor(n-1)}$ (vector) and the stacking functions $P_{i,j}$, determined using the previously defined functions with widths of time difference intervals $\delta t_{i,j}$, step S3 is used to provide an output Emp (which is a vector), using a calculation that is also made in a single step:

$$Emp(k) = \sum_{i=1}^{Nc} \sum_{j=i}^{Nc} P_{i,j}(k)$$

where:

$$P_{i,j}(k) = 1 - [1 - 2 \times \delta t_{i,j}(k)/T_{expo}]^{Spcor_{(n-1)}(E_i) \times Spcor_{(n-1)}(E_j)}$$

$Sp_{cor(n-1)}$ has already been defined above and $\delta_{i,j}(k)$ is the function that was presented above and that can be calculated according to one of the previously mentioned methods, and preferably using equation (1).

The correction of stacks (step S4) is made from vector $Sp_{mes}$ (or $Sp_{cor(n-1)}$ if there has been more than one iteration), the real number P and the vector Emp determined in S3. The result is an output $Sp_{cor(n)}$. The calculation is made in a single step:

$$Sp_{cor(n)} = \frac{Sp_{cor(n-1)} - Emp}{1 - P_{mean}}$$

Therefore step S4 subtracts the stacked spectrum from the measured spectrum. It may include a division by a factor that depends on the mean stacking probability $P_{mean}$ of the corrected spectrum $Sp_{cor}$, this factor may be equal to $1-P_{mean}$. If this division is not made, the shape of the spectrum will be kept but the integral will be kept.

If $N_{it}$ iterations have been made, the method stops and the last spectrum obtained $Sp_{cor(Nit)}$ is considered to be the required corrected spectrum. Otherwise, the method is started again, using the last obtained spectrum $Sp_{cor(n-1)}$ as the initial spectrum.

In each iteration, the calculations particularly of $P_{i,j}(k)$ and $Emp(k)$ are made as a function of the corrected spectrum obtained during the previous iteration (except the first iteration in which $P_{i,j}(k)$ and $Emp(k)$ are calculated as a function of the measured spectrum).

The larger the number $N_{it}$, the more precise the result will be. This number will be between 1 and 100, and preferably between 2 and 10, depending on the experimental results obtained.

The method of estimating the stacking function is based on the assumption that stacks with two photons are in the majority compared with stacks with three or more photons. This assumption is justified particularly for low fluxes (low stack rate).

For an incident photon, the stacking probability with one and only one photon can be written as follows:

$P_2=P_0(1-P_0)^n \times n$

Remember that the mean stacking probability can be written as follows:

$P_{mean}=1-(1-P_0)^{N-1}$

Consider the example of a system coupling a photon sensor followed by processing electronics for which the global dead time, namely the minimum time interval separating 2 photons absorbed in the sensor to measure them, is 62 ns.

Figure 12:
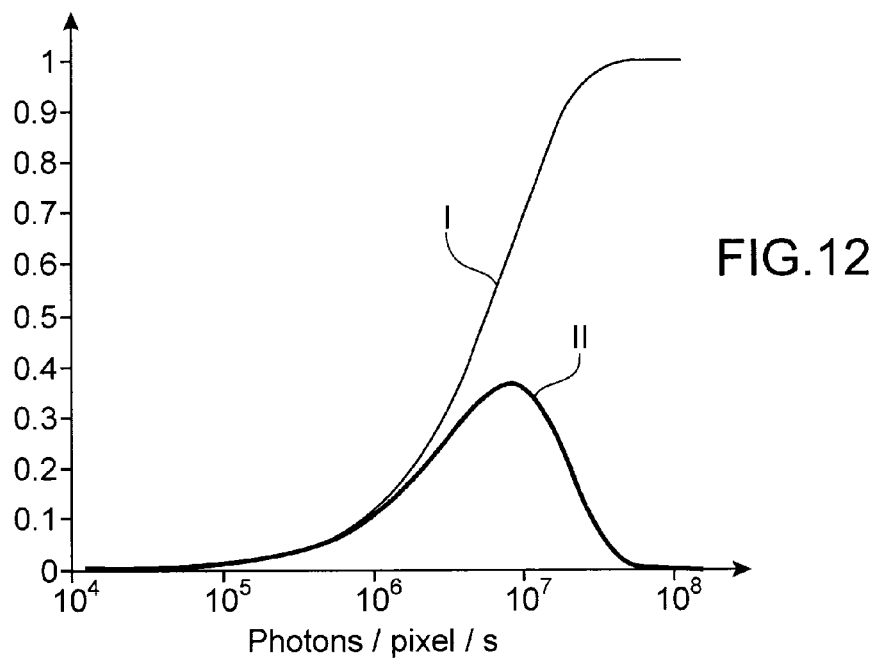
FIG. 12 shows simulated stacking probability curves for a dead time of 62 ns.

FIG. 12 shows variations in P and $P_2$, defined above as a function of the incident flux, expressed as a number of photons per pixel and per second.

The probability of stacking with two photons (curve II) is an increasing function of the flux for low values of the flux.

It then reaches a maximum before tending towards 0 for very high fluxes more than $5 \times 10^7$ photons/pixel/s.

On the other hand, the stacking probability P (curve I) is an increasing function of the flux. In the high flux zone, the stacking probability tends towards 1 and all stacks are stacks with more than two photons.

Figure 13:
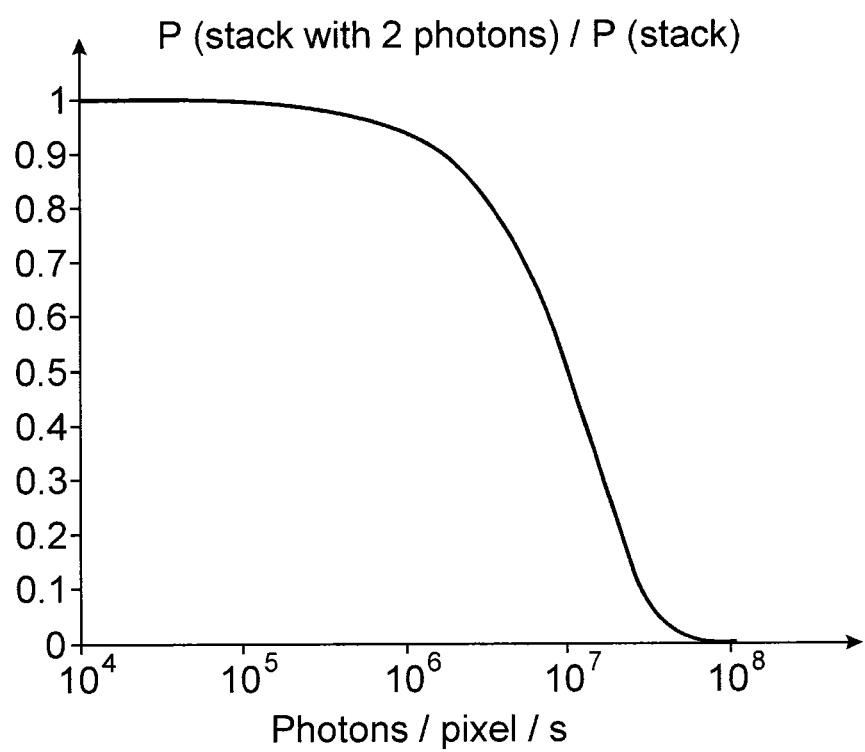
FIG. 13 shows a curve of the ratio of the stacking probability with two photons and the total stacking probability, for a dead time of 62 ns.

FIG. 13 shows the ratio between the probability of stacking with two photons and the total stacking probability.

This curve shows that the assumption is accurate within 1% throughout the range [0–5×10$^5$ photons/pixel/s].

It remains true within 7% for a flux of 1×10$^6$ photons/pixel/s.

Note that the flux range on which the assumption of stacking with two photons is accurate increases as the dead time of the system reduces.

Figure 14A:
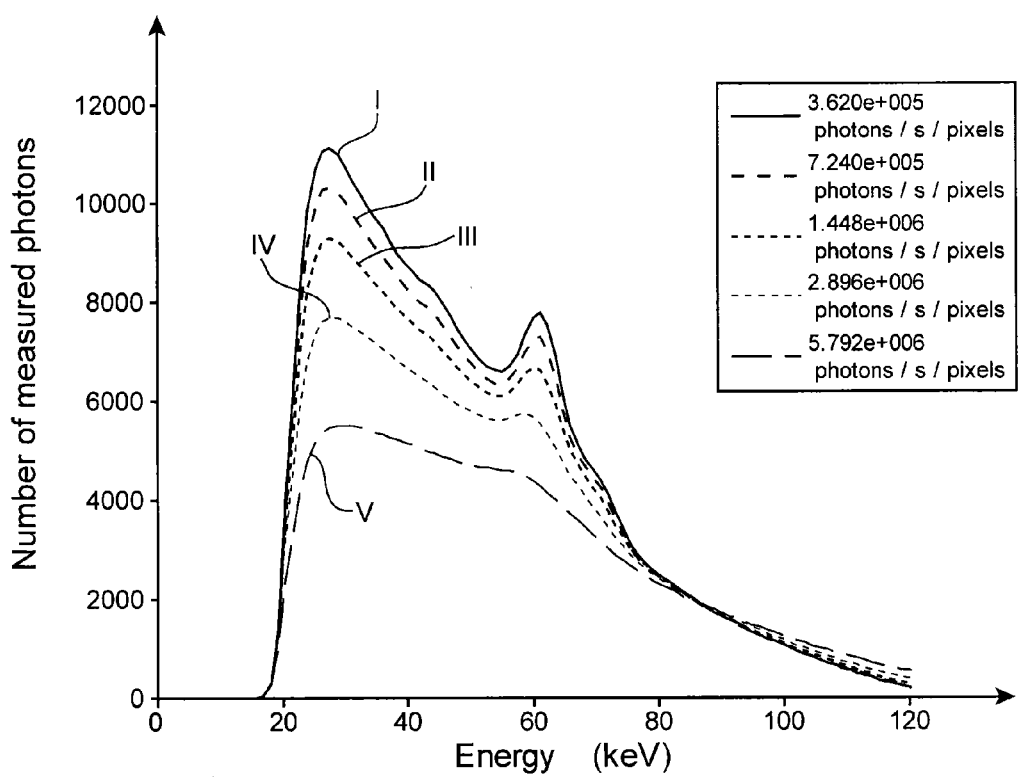
FIGS. 14A and 14B are spectrum measurements at different fluxes, before and after correction according to the invention respectively.
Figure 14B:
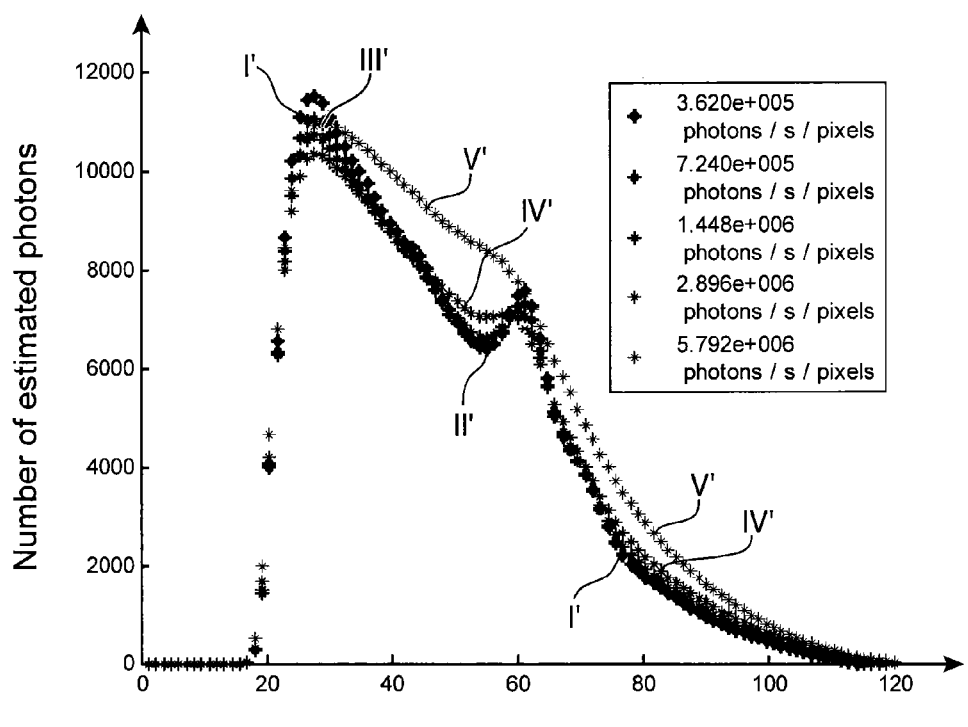

FIGS. 14A-14B show performances of the stacking correction method according to the invention, in fast spectrometry.

FIG. 14A shows measured spectra for different photon fluxes:
curve I: 3.62×10$^5$ photons/s/pixel,
curve II: 7.24×10$^5$ photons/s/pixel,
curve III: 1.448×10$^6$ photons/s/pixel,
curve IV: 2.896×10$^6$ photons/s/pixel,
curve V: 5.792×10$^6$ photons/s/pixel, FIG. 14B shows the same spectra after correction (the spectrum I' being the corrected spectrum of spectrum I, . . . etc) in 3 iterations.

These figures show good correction up to about 3×10$^6$ photons/s/pixel and degradation of the acquired corrected spectrum with a flux of about 6×10$^6$ photons/s/pixel, although the result is still acceptable.

The complete calibration is relatively simple. It can be done using a series of full flux measurements for different intensities of the X generator.

In the special embodiment of the invention described above, the determination of stacking functions with two photons does not require any additional calibration and can be based on a model based on knowledge of the dead time alone.

Therefore, the invention discloses a fast correction method that has the advantage that its only inputs are the data in the $Sp_{mes}$ spectrum and the $T_{expo}$ and $T_{dead}$ data. Therefore, this reduces the quantity of data to be transmitted to means performing the data processing.

Such a spectrum correction method can be implemented by the means 12 already described above.

These means are then programmed to store and process spectrum data and data to implement a method according to the invention, for example the $T_{expo}$ and $T_{dead}$ data.

The central processing unit 16 can thus be programmed to calculate a stacked spectrum, for example using an iterative method like that described below with reference to FIG. 11, and to calculate or estimate a corrected spectrum ($Sp_{cor}$) by taking the difference between stored measured spectrum data ($Sp_{mes}$) and stored stacked spectrum data (Emp).

These means 12 can also be used to make an estimate of the dead time $T_{dead}$ and/or the stacking function or its inverse function $\delta t_{i,j}(k)$, either experimentally or by modelling as explained above.

An operator can use means 12 to select one or several parameters to perform these operations.

In particular, he can select a number of iterations $N_{it}$ to perform an iterative method according to the invention.

A measured spectrum $Sp_{mes}$ and a corrected spectrum $Sp_{cor}$ according to this invention, and possibly a stacked spectrum Emp can be displayed on a screen or the display means 17. For example, an operator can use a pull down menu to choose a number of iterations to be made for processing according to the invention.

We will now describe several circuits that can be used within the scope of the invention, once again to deal with the problem of stacks as explained above.

Such a device advantageously allows high flux spectrometric measurements and can be used to extract values used for construction of the spectrum, even in the presence of many pulse stacks shaped by the delay line. It is advantageously combined with the method described above with reference to FIGS. 8-14.

Figure 15:
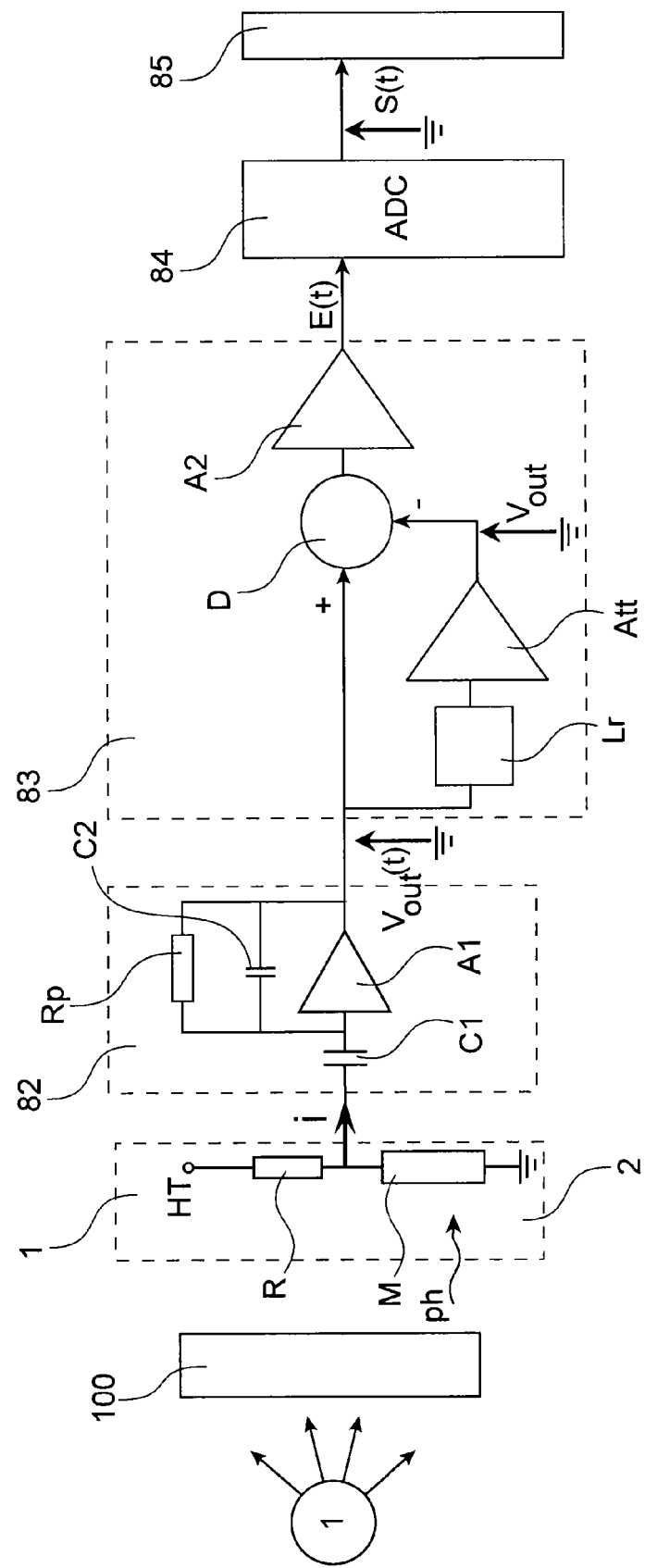
FIG. 15 shows an ionising electromagnetic radiation spectrometry detection device according to one embodiment of the invention.
Figure 16:
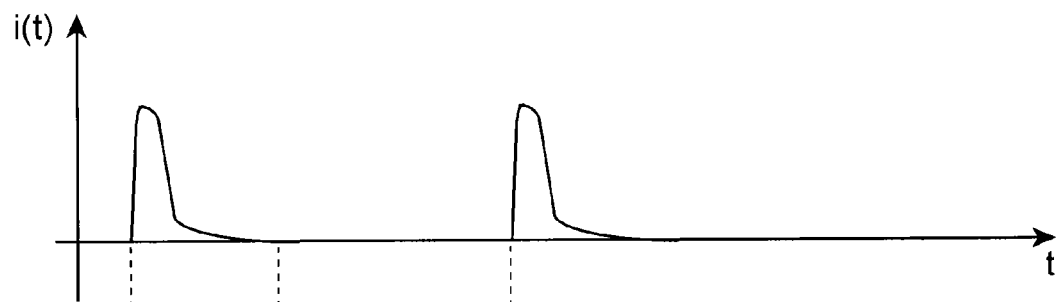
FIGS. 16 and 17 show characteristic electrical magnitudes at the output from the circuit 82 in FIG. 15.

FIG. 15 shows such an ionising electromagnetic radiation spectrometry detection device. In this figure, references 1 and 100 have the same meaning as in FIG. 1A. This device comprises the detector 2 (for example of the type described above) symbolised by a block of semiconducting material M and a resistance R that connects the block M to the HV high voltage. The electronic proximity circuit 2 is a charge pre-amplifier that includes a capacitance C1, an amplifier A1, a capacitance C2 and a resistance Rp. The capacitance C1 is installed at the input to the amplifier A1 and the capacitance C2 and the resistance Rp are mounted in series between the amplifier A1 input and output.

Figure 17:
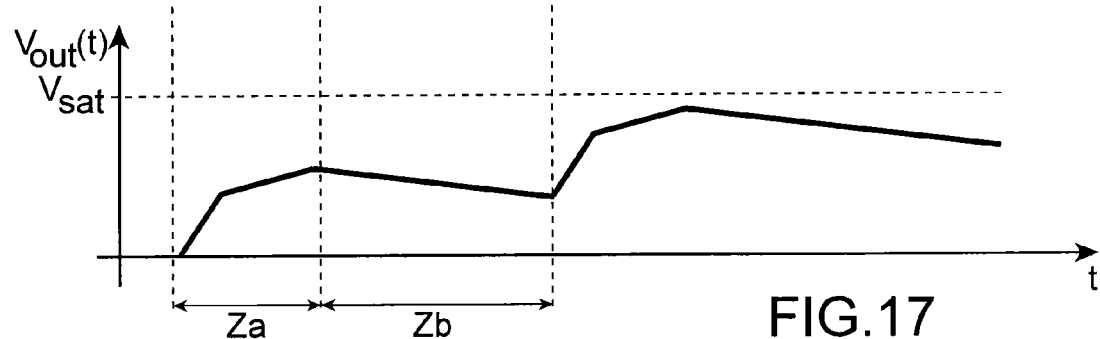

When an interaction of a photon is detected in a detector, the voltage $V_{OUT}(t)$ at the output from the charge pre-amplifier as long as the detector current i(t) output by the detector 1 is present, is equal to:

$$V_{OUT} = -\frac{1}{C2}\int i\,dt,$$

namely $$V_{OUT} = -\frac{Q}{C2}$$

where Q is the quantity of charge emitted by the photon that interacts in the semiconducting material M (see time zone Za in FIG. 17).

At the output from the charge pre-amplifier, the data corresponding to the photon energy is intermittent because the pre-amplifier discharges.

Therefore, this voltage has to be saved as quickly as possible after disappearance of the detector current (see time zone Zb in FIG. 17). At the same time, relaxation of the charge preamplifier provides a means of handling high count rates because the voltage at the output from the charge preamplifier accumulates, and without relaxation, the pre-amplifier would be quickly saturated (see the saturation voltage $V_{sat}$ in FIG. 17).

The voltage $V_{OUT}(t)$ output by the electronic circuit 82 is the input voltage to an electronic processing circuit 83.

The circuit 82 outputs the voltage E(t) (FIG. 10). The ADC then digitises E(t) to give a digitised signal, which corresponds to the points visible in FIG. 20.

Naturally, the invention can be applied to any other electronic processing circuit 83 capable of outputting an analogue pulse with an amplitude proportional to the energy deposited by an interaction in the detector, for example such as a peak detector or a switched active integrator like those mentioned above in prior art.

Having said this, the electronic processing circuit 83 described below corresponds to a preferred mode.

The output from the charge pre-amplifier 82 is directly connected to an assembly composed of a delay line Lr, an attenuator Att (gain less than 1), a subtractor D, an amplifier A2 and an analogue/digital conversion circuit ADC. The delay line Lr is mounted in series with the attenuator Att and forms a delay and transmission block, the first terminal of which is connected to the output from the preamplifier and the second terminal is connected to a first input to the subtractor D, the second input of which is connected directly to the output from the pre-amplifier.

The signal $V_{OUT}(t)$ output from the pre-amplifier is delayed through the delay line Lr, the delay of which is greater than the rise time of the $V_{OUT}(t)$ signal. The subtractor D subtracts the delayed and attenuated voltage $V_{OUT}(t)$ from the voltage $V_{OUT}(t)$ and the amplifier A2 amplifies the signal resulting from this subtraction and then outputs an analogue pulse E(t) through the amplifier A2, the magnitude of the pulse being proportional to the energy deposited by the detected photon.

Figure 20:
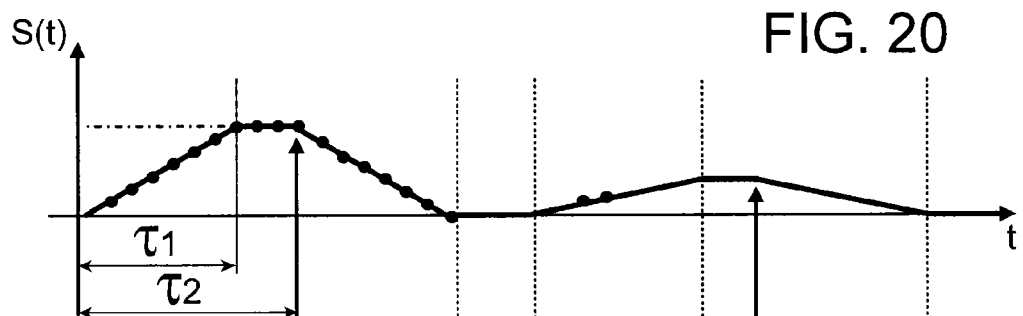

The digitisation made by the analogue/digital converter ADC 34 is done continuously since the computer is programmed to identify energy values greater than a predetermined energy threshold $E_S$. The result of this digitisation is shown in FIG. 20: each analogue pulse is replaced by a digitised signal pulse which assembles a series of digital signals S(t) represented by dots in FIG. 20. Thus, a digitised pulse assembles all digital signals S(t) produced by processing the analogue pulse E(t) by the analogue digital converter.

The device also comprises a circuit 85 that performs processing of the digital signals S(t) output by the analogue/digital converter ADC.

Figure 18:
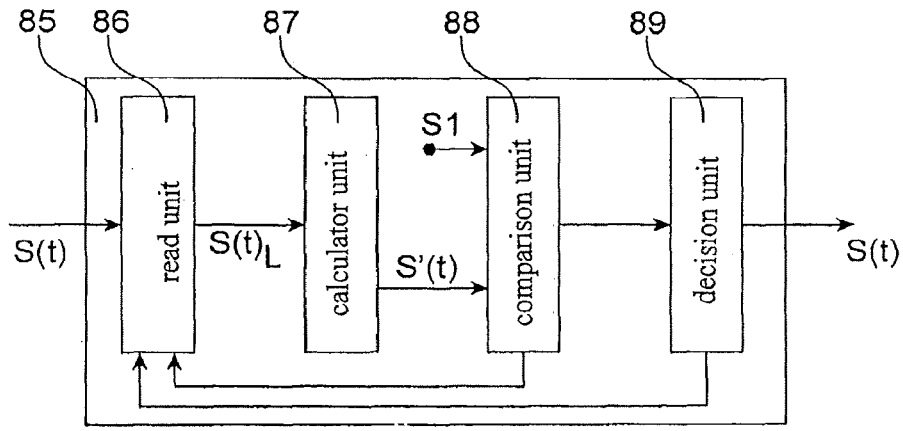
FIG. 18 shows a detailed view of a circuit in the detection device according to the invention shown in FIG. 15, FIGS. 20 and 21 show electrical signals characteristic of the circuit shown in FIG. 18.

FIG. 18 explicitly shows processing units of the circuit 85 that operate within the scope of the invention.

Figure 19:
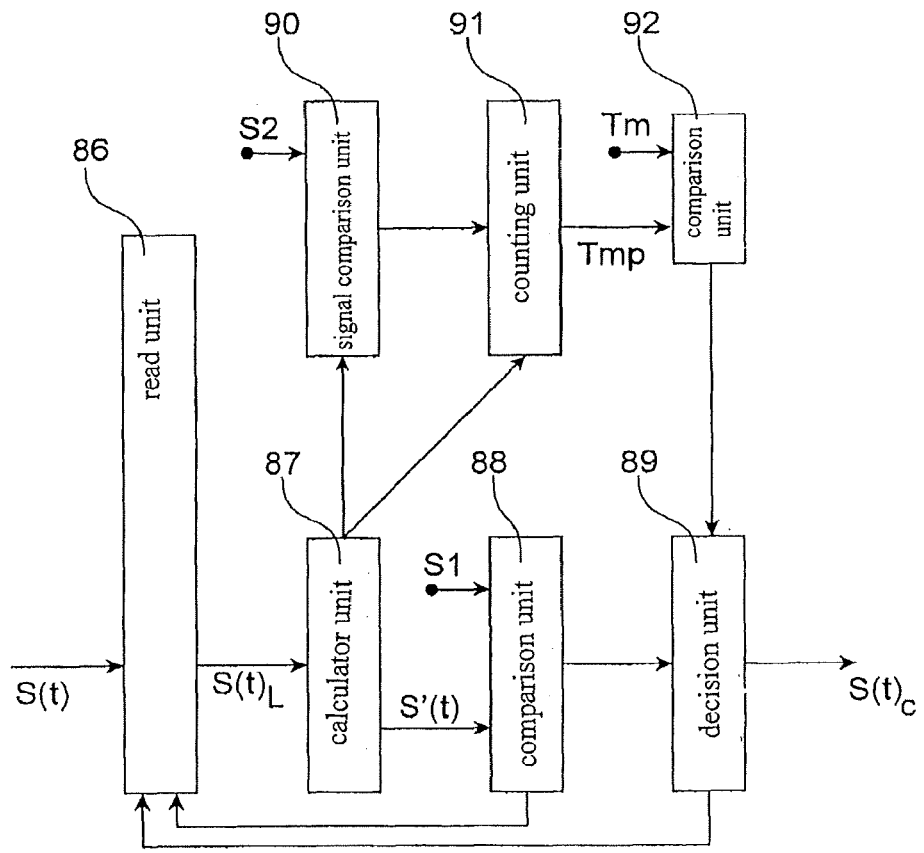
FIG. 19 shows an improvement to the circuit shown in FIG. 18, FIGS. 22A and 22B show electrical signals characteristic of the circuit in FIG. 18 that show operation of the device according to the invention in the presence of a large number of stacks.

FIG. 19 shows an improvement to the circuit in FIG. 18.

For example, the circuit 85 may be a microprocessor or a Field Programmable Gate Array (FPGA), or an Application Specific Integrated Circuit (ASIC).

According to the preferred embodiment of the invention, the circuit that outputs a pulse uses a delay line which advantageously can give a pulse for which the time characteristics (rise time, fall time) are similar to the pulse collected by the electrode of the detector.

The use of a delay line circuit can thus give precise time information.

FIG. 18 shows processing units of the circuit 85. The computer 85 comprises a unit 86 to read the digitised signal S(t) output by the analogue/digital converter ADC, a unit 87 to calculate the rate of time variation S'(t) between two successive digital signals $S_L(t)$ read, a unit 88 to compare the time variation rate S'(t) output by the unit 87 with a predetermined variation threshold S1 and a unit 89 that decides on whether or not the read digital signal has to be captured.

Figure 21:
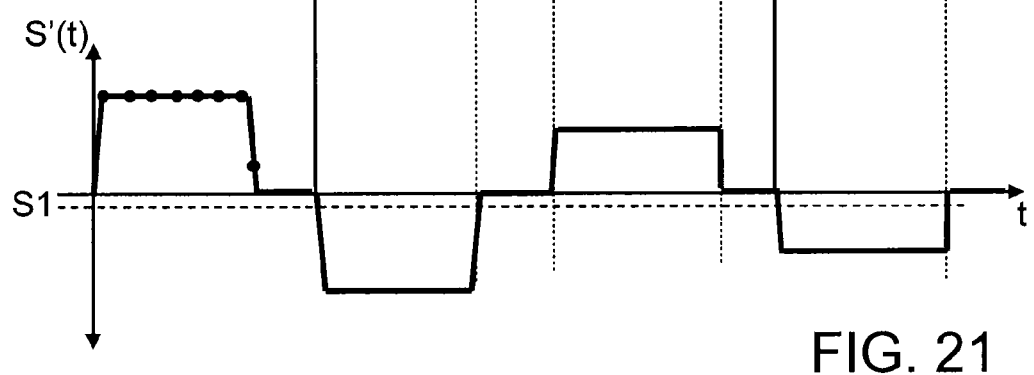

The read unit 86 reads the digital signal S(t) output by the analogue/digital converter AD at a read frequency $f_L$ preferably equal to the sampling frequency of the analogue digital converter ADC, the read unit and the analogue digital converter then being synchronised by the same clock. FIG. 21 shows an example of digital signals output by the analogue/digital converter ADC forming discretisation of analogue pulses E(t), this discretisation generating digitised signal pulses.

The signal output by the analogue/digital converter ADC is continuously digitised, for example at a high frequency between 1 MHz and 1 GHz (typically a few hundred MHz). The time τ1 shown in FIG. 21 corresponds to the rise time of the analogue pulse (charge transit time in the detector), and the time τ2 corresponds to the duration between the beginning of the analogue pulse and its decay (τ2 can thus be equal to the dead time of the spectrometry system used).

The read unit 86 outputs a read digital signal $S(t)_L$. The unit 87 that calculates the time variation rate then determines the variation rate S'(t) in the form of the following equation (1):

$$S'(t)=[S(t)_L-S(t-dt)_L]/dt \qquad (1)$$

Thus, a variation rate S'(t) may be calculated at each new pulse read $S_L(t)$, in other words at the read frequency, usually equal to the sampling frequency of the analogue digital converter.

FIG. 21 shows the digital signal output by the unit that calculates the time variation rate when the digital signal output by the ADC converter is conforming with the signal shown in FIG. 13, as an example.

The variation rate S'(t) output by the unit 87 is compared with the threshold S1 by the comparison unit 88.

At the time of each pulse of the digitised signal read $S_L(t)$, the signal S'(t) successively describes a first part corresponding to the growth in the amplitude of the signals $S_L(t)$, and a second part corresponding to the decay in the amplitude of the read digitised signals $S_L(t)$.

In this case, the first part can be called the positive part because it corresponds to positive values of S'(t). Similarly, the second part may be called the negative part because it corresponds to negative values of $S_L(t)$.

The threshold S1 is usually set to a predetermined negative value.

The absolute value of the threshold S1 is chosen such that it is greater than the amplitude of the noise BS'(t) affecting the variation rate S'(t). Values of the variation rate S'(t) are affected by high frequency fluctuations that can be of the same order of magnitude as the sampling frequency, due to the noise $BS_L(t)$ affecting the read digital signal $S_L(t)$. The average value of the noise BS'(t) is usually zero. The threshold S1 is set to a negative value such that the absolute value of S1 is greater than the maximum noise amplitude BS'(t), but also such that the absolute value of S1 is low enough so that when S'(t) reaches this threshold, the signal $S_L(t)$ corresponds approximately to a local maximum, in other words is as close as possible to the maximum value of a pulse, as can be seen in FIGS. 22A and 22B. As close as possible means a few periods dt of the synchronisation clock. The adjustment step of the threshold S1 is made experimentally and can be renewed, such that the value of the threshold S1 can be refreshed.

The comparison signal output by the comparison unit 88 controls the decision unit 89. If the threshold S1 is not crossed (i.e. S1≤S'(t)), the comparison signal controls the decision unit such that the last digital signal read is not captured. If the threshold is crossed, i.e. S'(t)≤S1), the comparison signal controls the decision unit such that the last read pulse $S_L(t)$ is captured.

Once the capture has or has not been made, another digital signal is read.

The first part (or positive part) of the signal S'(t) corresponds to the image of the photonic current pulse obtained by interaction of a photon in the detector.

The second part (or negative part) of the signal S'(t) is used for synchronisation: when this negative part is crossed, the corresponding value of the signal $S_L(t_0)$ is retained for formation of the spectrum, $t_0$ corresponding to the instant at which $S'(t_0)$ drops below the threshold S1. Thus, $t_0$ is such that $S'(t_0-dt)>S1$ at $t_0-\delta t$, and $S'(t_0)\leq S1$ at $t_0$, dt being the period of the read circuit synchronisation clock.

Advantageously, the device according to the invention gives better discrimination of coincident interactions than the discrimination obtained by circuits according to prior art.

The fact of working on the variation with time of the signal present on the downstream side of the delay line has an advantage over working on the variation with time of the signal present on the upstream side of this line. The filter effect of the delay line is useful, the signal to noise ratio of the signal present at the output from the delay line being better than that existing at the input to the line.

The time information obtained is more precise.

FIG. 19 shows an improvement to the circuit shown in FIG. 18. According to this improvement, the device comprises means capable of determining a duration of the positive part of the signal S'(t). When S'(t) reaches the value S1, but the positive part of S'(t) exceeds a predetermined duration Tm, the capture is not made. The positive part of S'(t) means all signals S'(t) determined during the rise in amplitude of the signals $S_L(t)$ during the same digitised analogue pulse.

Apart from the circuits 86, 87, 88 and 89 mentioned above, the circuit 5 comprise a signal comparison unit 90, a unit counting the duration of the positive part of S'(t) 91 and a unit comparing the duration of this positive part 92. The signal S'(t) is firstly compared with a threshold value S2. The threshold value S2 is chosen such that its sign is opposite to S1 and its absolute value is greater than the maximum noise amplitude BS'(t). It may have a value opposite to S1, in other words the same absolute value but with an opposite sign. When the signal S'(t) is greater than S2, the comparator 40 outputs a signal that controls the count of the pulse duration $T_{imp}$, otherwise there is no count.

The pulse duration counter is incremented for each digital value read S'(t) until a signal S'(t) becomes less than S2, which stops the count of the pulse duration $T_{imp}$.

The duration $T_{imp}$ of the positive part of the pulse S'(t) output by the count unit 11 is then compared with a threshold value with duration $T_m$. The duration $T_m$ is preferably chosen as being the rise time of the signal at the output from the charge pre-amplifier. If the pulse duration $T_{imp}$ is greater than $T_m$, the signal output by the comparator 82 controls the decision unit 89 so that it does not capture the signal $S_L(t_0)$ corresponding to the instant $t_0$ at which S'(t) crosses the threshold S1.

If the pulse duration $T_{imp}$ is less than or equal to $T_m$, the signal $S_L(t_0)$ corresponding to the instant $t_0$ at which S'($t_0$) ≤S1 and S'($t_0$−dt)>S1, where δt is the period of the read circuit synchronisation clock, is taken into account.

The device according to the invention advantageously authorises high flux spectrometric measurements; it can extract the values used for construction of the spectrum even in the presence of many pulse stacks shaped by the delay line. FIGS. 22A and 22B show this advantage of the invention. FIG. 22A shows voltage pulses obtained in the presence of many stacks and FIG. 22B shows variations with time of the voltage stacks shown in FIG. 22A.

Crossing of the threshold S1 by variations with time of the signal (see FIG. 22B) gives a time marker to trigger saving in the spectrum of the signal. As soon as the variation with time drops below the threshold S1 (see FIG. 22B), the corresponding value of the signal (see FIG. 22A) is marked and saved for building up the spectrum.

Unlike methods according to prior art, it is always possible to extract correct measurements, even when pulses are superposed.

The device according to the invention can thus increase the performances of pulse shaping systems, to the maximum of their count rate performances.

FIGS. 23A and 23B show the advantages resulting from the improvements to the device according to the invention according to FIG. 19.

If the duration of the positive part of the variation with time of the signal is longer than the reference time $T_m$, then stacking occurs. The detected energy value corresponding to the signal $S_L(t)$ captured is then distorted and it must not be included in the energy spectrum.

FIGS. 23A and 23B show the case in which two photons interact in the detector within a very short time. In this case the variation with time of the signal does not cross the threshold S1 and the duration of the positive part of the variation with time is more than $T_m$. Therefore, the two photons are not selected for the spectrum.

The dead time of the delay line device according to the invention is the time necessary to measure the energy of a photon that interacts in the detector, in other words the delay $T_d$ imposed by the delay line. One condition to be respected in the device according to the invention is that the delay $T_d$ is greater than or equal to the duration $T_m$.

In particular, the invention relates to the field of material analysis techniques, for example to identify a product such as an explosive in a traveller's luggage, using the analysis of the X-radiation transmission function of this luggage. Therefore, it also relates to a method to identify the nature of a material in luggage, or to investigate the content of luggage, including positioning the luggage on the path of a beam such as the beam 200 and detection of transmitted radiation for example using the device in FIG. 1A. Use of a method according to the invention can then identify whether or not there is any explosive present in the luggage. Therefore, it has applications in systems used in airports to identify explosive materials in luggage.

The invention claimed is:

1. A method for providing an improved characterization of a nature of a material and/or of a thickness of the material, comprising:

providing at least one object comprising the material between an X-ray source and a single detector;

using the X-ray source, obtaining at least one X-radiation spectrum of radiation transmitted through the object and impinging on the single detector for a time between about 1 ms and about 10 seconds and for a minimum fluence rate of incident photon radiation that is about $10^6$ mm$^{-2}$s$^{-1}$ to about $10^7$ mm$^{-2}$s$^{-1}$, the at least one X-radiation spectrum of radiation representing an amplitude distribution of radiation pulses measured by the detector;

calculating, from the obtained at least one X-radiation spectrum, a transmission function of the material as a function of energy or of energy channel, from a ratio of an intensity of the radiation transmitted through the object to an intensity of radiation that is incident on the object;

selecting N different energy bands from the obtained at least one X-radiation spectrum for the calculated transmission function, N being greater than or equal to 2;

calculating, via at least one circuit or processor, a transmission coefficient corresponding to each of the selected N different energy bands by applying a statistical magnitude of the calculated transmission function in each of the selected N different energy bands, said statistical magnitude being obtained by calculating an integral or an average of the calculated transmission function in a given energy band of said selected N different energy bands, and said calculated transmission coefficient comprising a first transmission coefficient α1 corresponding to a first energy band of the selected N different energy bands and a second transmission coefficient α2 corresponding to a second energy band of the selected N different energy bands, said first and second transmission coefficients comprising coordinates (α1, α2) in an (α1, α2) plane; and providing the improved characterization of the nature of the material and/or the thickness of the material, via the at least one circuit or processor, by comparing values of the coordinates (α1, α2) in the (α1, α2) plane with values of known coordinates of standard transmission coefficients ($\alpha_{standardmaterial1}$, $\alpha_{standardmaterial2}$) in the (α1, α2) plane.

2. The method according to claim 1, wherein the intensity of the radiation that is incident on the object is determined either in an absence of the object, or by calculation based on known emission parameters of the source.

3. The method according to claim 1, wherein N is equal to 2, the method further comprising:

selecting a first energy zone as a low energy zone corresponding to the first energy band, and a second energy zone as a high energy zone corresponding to the second energy band, wherein the calculating the integral or the average of the calculated transmission function is with respect to energy in order to obtain said statistical magnitude.

4. The method according to claim 3, wherein the first energy zone is between 15 keV and 50 keV, and the second energy zone is between 50 keV and 120 keV.

5. The method according to claim 1, wherein the minimum fluence rate of incident photon radiation is greater than $10^7$ mm$^{-2}$s$^{-1}$.

6. The method according to claim 1, wherein a number of the at least one radiation spectrum obtained is between 1 and 100.

7. The method according to claim 1, wherein the providing the improved characterization of the nature and/or of the thickness of the material comprises using the calculated transmission coefficients corresponding to said each of the selected N different energy bands by positioning the calculated coefficients in a plane comprising known material coefficients as a function of their thickness.

8. The method according to claim 1, wherein the comparison between the values of the coordinates (α1, α2) in the (α1, α2) plane with values of known coordinates of standard transmission coefficients ($\alpha_{standardmaterial1}$, $\alpha_{standardmaterial2}$) in the (α1, α2) plane comprises a measurement of distance between a set of N transmission coefficients and each standard set of N transmission coefficients of each standard material, the nature of the material and/or the thickness of the material corresponding to a nature and/or a thickness of the standard material represented by the standard set of N transmission coefficients having closest coordinates.

9. The method according to claim 1, further comprising a prior step of measuring an energy spectrum of radiation from the X-ray source when there is no material inserted between the source and the single detector.

10. The method according to claim 1, further comprising a spectrum correction for disturbances resulting from stacking phenomena.

11. The method according to claim 1, wherein the detector comprises a detector made of a CdTe or CdZnTe or CdMnTe, or HgI2, or AsGa, or Si, or TlBr semiconductor.

12. A device for the providing an improved characterization of a nature of a material and/or of a thickness of the material, comprising:

an X-ray source;

a single detector and an electronic circuit configured to obtain at least one X-radiation spectrum transmitted through an object comprising the object and impinging on the single detector for a time between about 1 ms and about 10 seconds and for a minimum fluence rate of incident photon radiation that is about $10^6$ mm$^{-2}$s$^{-1}$ to about $10^7$ mm$^{-2}$s$^{-1}$, the at least one X-radiation spectrum of radiation representing an amplitude distribution of radiation pulses measured by the detector; and at least one processing circuit configured to:

calculate, from the obtained at least one X-radiation spectrum, a transmission function of the material as a function of energy or of energy channel, from a ratio of an intensity of the radiation transmitted through the object to an intensity of radiation that is incident on the object, calculate at least one transmission coefficient corresponding to each of N different selected energy bands from the obtained at least one X-radiation spectrum for the calculated transmission function, N being greater than or equal to 2, by applying a statistical magnitude of the calculated transmission function in each of the selected N different energy bands, said statistical magnitude being obtained by calculating an integral or an average of the calculated transmission function in a given energy band of said selected N different energy bands, said calculated at least one transmission coefficient comprising at least a first transmission coefficient α1 corresponding to a first energy band of the selected N different energy bands and a second transmission coefficient α2 corresponding to a second energy band of the selected N different energy bands, said first and second transmission coefficients comprising coordinates (α1, α2) in an (α1, α2) plane, and provide the improved characterization of the nature of the material and/or the thickness of the material by comparing values of the coordinates (α1, α2) in the (α1, α2) plane with values of known coordinates of standard transmission coefficients ($\alpha_{standardmaterial1}$, $\alpha_{standardmaterial2}$) in the (α1, α2) plane.

13. The device according to claim 12, wherein the intensity of the radiation that is incident on the object is determined either in an absence of the object, or by calculation based on known emission parameters of the source.

14. The device according to claim 12, wherein N is equal to 2, the at least one processing circuit being further configured to calculate the integral or the average of the calculated transmission function with respect to energy, and to select a first energy zone as a low energy zone corresponding to the first energy band, and a second energy zone as a high energy zone corresponding to the second energy band.

15. The device according to claim 12, wherein the X-ray minimum fluence rate of incident photon radiation emitted from the X-ray source is greater than $10^7$ mm$^{-2}$s$^{-1}$.

16. The device according to claim 12, wherein the single detector comprises a detector made of a CdTe or CdMnTe, or HgI2, or AsGa, or Si, or TlB semiconductor.

17. The device according to claim 12, wherein the at least one processing circuit is further configured to correct the at least one X-radiation spectrum for disturbances resulting from a stacking phenomenon.

18. The device according to claim 17, wherein the at least one processing circuit is further configured to:
determine a stacked spectrum, which is a part of the obtained at least one X-radiation spectrum, and which corresponds to stacks alone, and
calculate at least one first corrected spectrum, by taking a difference between the obtained at least one X-radiation spectrum and the stacked spectrum.

19. The device according to claim 18, wherein the stacked spectrum is calculated using the obtained at least one X-radiation spectrum and exposure time and dead time data for the device, a minimum time separating two photons below which only one of the two photons is detected.

20. The device according to claim 12, further comprising:
a circuit configured to output a voltage pulse for which amplitude is proportional to a charge detected by the single detector;
an analog/digital converter configured to digitize the voltage pulse and to output a digital pulse, and including a processing circuit on an output side of the analog/digital converter being configured to:
read digital pulses output by the analogue/digital converter, at a read frequency,
calculate a time variation of the digital pulses read, and capture digital pulses for which the time variation reaches a predetermined threshold.

* * * * *